US008623301B1

(12) United States Patent
Deininger et al.

(10) Patent No.: US 8,623,301 B1
(45) Date of Patent: Jan. 7, 2014

(54) SOLID OXIDE FUEL CELLS, ELECTROLYZERS, AND SENSORS, AND METHODS OF MAKING AND USING THE SAME

(75) Inventors: Mark Deininger, Roswell, GA (US); Mikhail Pozvonkov, Cumming, GA (US); Paul Fisher, Landis, NC (US); Leonid V. Budaragin, Moscow (RU); D. Morgan Spears, Atlanta, GA (US)

(73) Assignee: C3 International, LLC, Alpharetta, GA (US)

( * ) Notice: Subject to any disclaimer, the term of this patent is extended or adjusted under 35 U.S.C. 154(b) by 714 days.

(21) Appl. No.: 12/420,457

(22) Filed: Apr. 8, 2009

Related U.S. Application Data

(60) Provisional application No. 61/043,566, filed on Apr. 9, 2008.

(51) Int. Cl.
*C01F 17/00* (2006.01)
*H01M 8/10* (2006.01)

(52) U.S. Cl.
USPC ........... 423/21.1; 429/491; 429/495; 429/496

(58) Field of Classification Search
None
See application file for complete search history.

(56) References Cited

U.S. PATENT DOCUMENTS

| | | | |
|---|---|---|---|
| 2,048,912 A | 7/1936 | Ziska et al. |
| 2,141,477 A | 12/1938 | Loesch |
| 2,334,294 A | 11/1943 | Stevens |
| 2,470,796 A | 5/1949 | Stromquist |
| 2,530,110 A | 11/1950 | Woodyard |
| 2,551,722 A | 5/1951 | Bowen |
| 2,631,356 A | 3/1953 | Sparks et al. |
| 2,792,807 A | 5/1957 | Cummings |
| 2,800,875 A | 7/1957 | Jewell |

(Continued)

FOREIGN PATENT DOCUMENTS

| | | |
|---|---|---|
| DE | 295148 A5 | 10/1991 |
| EP | 85307586.9 A1 | 10/1985 |

(Continued)

OTHER PUBLICATIONS

Xu, Zhigang; Wei, Q.; Sankar, Jag, Preparation and properties of YSZ electrolyte thin films via liquid fuel combustion chemical vapor deposition, NSF Center for Advanced Materials and Smart Structures, North Carolina A and T State, Ceramic Engineering and Science Proceedings, (2002), 23(3), 711-718.*

(Continued)

*Primary Examiner* — Cynthia K. Walls
(74) *Attorney, Agent, or Firm* — Thrive IP; Jeremy M. Stipkala

(57) ABSTRACT

The present invention provides solid oxide fuel cells, solid oxide electrolyzer cells, solid oxide sensors, components of any of the foregoing, and methods of making and using the same. In some embodiments, a solid oxide fuel cell comprises an air electrode (or cathode), a fuel electrode (or anode), an electrolyte interposed between the air electrode and the fuel electrode, and at least one electrode-electrolyte transition layer. Other embodiments provide novel methods of producing nano-scale films and/or surface modifications comprising one or more metal oxides to form ultra-thin (yet fully-dense) electrolyte layers and electrode coatings. Such layers and coatings may provide greater ionic conductivity and increased operating efficiency, which may lead to lower manufacturing costs, less-expensive materials, lower operating temperatures, smaller-sized fuel cells, electrolyzer cells, and sensors, and a greater number of applications.

15 Claims, 2 Drawing Sheets

(56) References Cited

U.S. PATENT DOCUMENTS

| | | | |
|---|---|---|---|
| 3,503,809 A | 3/1970 | Spacil |
| 3,516,385 A | 6/1970 | Walling |
| 3,673,452 A | 6/1972 | Brennen |
| 3,679,712 A | 7/1972 | Firestone |
| 3,773,555 A | 11/1973 | Cotton et al. |
| 3,947,292 A | 3/1976 | Jackovitz et al. |
| 3,962,490 A | 6/1976 | Ward |
| 3,967,149 A | 6/1976 | Eaton et al. |
| 3,984,717 A | 10/1976 | Romanowski et al. |
| 4,267,483 A | 5/1981 | Nakajima et al. |
| 4,297,150 A | 10/1981 | Foster et al. |
| 4,307,061 A | 12/1981 | Sarholz |
| 4,318,894 A | 3/1982 | Hensel et al. |
| 4,358,892 A | 11/1982 | Turillon et al. |
| 4,530,340 A | 7/1985 | Totman |
| 4,686,201 A | 8/1987 | Porter et al. |
| 4,687,567 A | 8/1987 | Porter et al. |
| 4,743,793 A | 5/1988 | Toya et al. |
| 4,774,905 A | 10/1988 | Nobis |
| 4,786,267 A | 11/1988 | Toya et al. |
| 4,826,462 A | 5/1989 | Lenk |
| 4,828,934 A | 5/1989 | Pinkhasov |
| 4,853,582 A | 8/1989 | Sato et al. |
| 4,881,913 A | 11/1989 | Mann |
| 4,898,197 A | 2/1990 | Barry et al. |
| 4,925,886 A | 5/1990 | Atkins et al. |
| 4,935,265 A | 6/1990 | Pike |
| 4,937,484 A | 6/1990 | Ishino |
| 4,961,917 A | 10/1990 | Byrne |
| 4,963,112 A | 10/1990 | Benedikt et al. |
| 4,963,390 A | 10/1990 | Lipeles et al. |
| 4,972,811 A | 11/1990 | Baresel et al. |
| 5,015,358 A | 5/1991 | Reed et al. |
| 5,021,398 A | 6/1991 | Sharma et al. |
| 5,028,467 A | 7/1991 | Maruyama et al. |
| 5,073,410 A | 12/1991 | Paz-Pujalt |
| 5,096,880 A | 3/1992 | Rybka |
| 5,100,632 A | 3/1992 | Dettling et al. |
| 5,106,706 A | 4/1992 | Singh et al. |
| 5,109,178 A | 4/1992 | Yoshida et al. |
| 5,130,210 A * | 7/1992 | Iwasaki et al. ............... 429/496 |
| 5,174,298 A | 12/1992 | Dolfi et al. |
| 5,230,842 A | 7/1993 | Munde |
| 5,274,298 A | 12/1993 | Cassidy et al. |
| 5,279,111 A | 1/1994 | Bell et al. |
| 5,312,585 A | 5/1994 | Jones |
| 5,342,703 A | 8/1994 | Kawasaki et al. |
| 5,395,896 A | 3/1995 | Moriya et al. |
| 5,413,642 A | 5/1995 | Alger |
| 5,423,285 A | 6/1995 | Paz de Araujo et al. |
| 5,468,679 A | 11/1995 | Paz de Araujo et al. |
| 5,472,795 A | 12/1995 | Aita |
| 5,494,700 A * | 2/1996 | Anderson et al. ............. 427/115 |
| 5,496,415 A | 3/1996 | Barnham |
| 5,518,603 A | 5/1996 | Furuhashi et al. |
| 5,551,994 A | 9/1996 | Schriever |
| 5,580,497 A | 12/1996 | Balachandran et al. |
| 5,601,869 A | 2/1997 | Scott et al. |
| 5,612,082 A | 3/1997 | Azuma et al. |
| 5,626,035 A | 5/1997 | Pozvonkov |
| 5,645,634 A | 7/1997 | Ogi et al. |
| 5,689,797 A | 11/1997 | Chelluri et al. |
| 5,699,035 A | 12/1997 | Ito et al. |
| 5,753,385 A | 5/1998 | Jankowski et al. |
| 5,805,973 A | 9/1998 | Coffinberry et al. |
| 5,817,436 A | 10/1998 | Nishijima et al. |
| 5,827,570 A | 10/1998 | Russell |
| 5,905,363 A | 5/1999 | Helbing et al. |
| 5,919,519 A | 7/1999 | Tallis |
| 5,924,158 A | 7/1999 | Watts |
| 5,952,769 A | 9/1999 | Budaragin |
| 5,968,463 A | 10/1999 | Shelef et al. |
| 5,976,458 A | 11/1999 | Sikka et al. |
| 5,990,416 A | 11/1999 | Windisch, Jr. et al. |
| 6,040,265 A | 3/2000 | Nunan |
| 6,051,529 A | 4/2000 | Brezny |
| 6,071,464 A | 6/2000 | Funaki et al. |
| 6,079,074 A | 6/2000 | Ellett |
| 6,093,378 A | 7/2000 | Deeba et al. |
| 6,117,581 A | 9/2000 | Shelef |
| 6,127,202 A | 10/2000 | Kapur et al. |
| 6,135,129 A | 10/2000 | Akazawa |
| 6,139,921 A | 10/2000 | Taschner et al. |
| 6,153,160 A | 11/2000 | Voss et al. |
| 6,190,634 B1 | 2/2001 | Lieber et al. |
| 6,224,993 B1 | 5/2001 | Hartvigsen et al. |
| 6,268,014 B1 | 7/2001 | Eberspacher et al. |
| 6,320,375 B1 | 11/2001 | Cotton et al. |
| 6,328,449 B1 | 12/2001 | Hacskaylo |
| 6,328,779 B1 | 12/2001 | He et al. |
| 6,379,712 B1 | 4/2002 | Yan et al. |
| 6,416,818 B1 | 7/2002 | Aikens et al. |
| 6,426,315 B1 | 7/2002 | Bergstrom et al. |
| 6,448,190 B1 | 9/2002 | Hayashi et al. |
| 6,454,492 B1 | 9/2002 | Dean et al. |
| 6,476,312 B1 | 11/2002 | Barnham |
| 6,500,733 B1 | 12/2002 | Stanbery |
| 6,559,372 B2 | 5/2003 | Stanbery |
| 6,593,213 B2 | 7/2003 | Stanberry |
| 6,620,456 B2 | 9/2003 | Blanton et al. |
| 6,624,213 B2 | 9/2003 | George et al. |
| 6,663,983 B1 | 12/2003 | Darolia et al. |
| 6,683,025 B2 | 1/2004 | Amendola et al. |
| 6,730,757 B2 | 5/2004 | Wang et al. |
| 6,736,986 B2 | 5/2004 | Stanberry |
| 6,769,152 B1 | 8/2004 | Crenshaw et al. |
| 6,773,513 B2 | 8/2004 | Ludtka |
| 6,824,883 B1 | 11/2004 | Benum et al. |
| 6,872,049 B2 | 3/2005 | Christensen |
| 6,899,966 B2 | 5/2005 | Benum et al. |
| 6,903,331 B2 | 6/2005 | Bateman et al. |
| 6,921,557 B2 | 7/2005 | Jacobson et al. |
| 6,969,484 B2 | 11/2005 | Horiguchi et al. |
| 6,998,187 B2 | 2/2006 | Finnerty et al. |
| 7,045,238 B2 | 5/2006 | Gottmann et al. |
| 7,083,710 B2 | 8/2006 | Scheer et al. |
| 7,105,807 B2 | 9/2006 | Hansen |
| 7,117,099 B2 | 10/2006 | Strassner et al. |
| 7,156,979 B2 | 1/2007 | Benum et al. |
| 7,161,124 B2 | 1/2007 | Kisner et al. |
| 7,163,759 B2 | 1/2007 | Milliken et al. |
| 7,177,099 B2 | 2/2007 | Mercado et al. |
| 7,211,292 B1 | 5/2007 | Budaragin |
| 7,227,172 B2 | 6/2007 | Kitaoka et al. |
| 7,227,736 B2 | 6/2007 | Shioga et al. |
| 7,229,597 B2 | 6/2007 | Patchett et al. |
| 7,235,171 B2 | 6/2007 | Taniguchi |
| 7,250,147 B2 | 7/2007 | Tour et al. |
| 7,255,956 B2 | 8/2007 | McElroy et al. |
| 7,271,333 B2 | 9/2007 | Fabick et al. |
| 7,279,047 B2 | 10/2007 | Melnik et al. |
| 7,300,684 B2 | 11/2007 | Boardman et al. |
| 7,306,823 B2 | 12/2007 | Sagar et al. |
| 7,318,763 B2 | 1/2008 | Tsakalakos et al. |
| 7,351,488 B2 | 4/2008 | Visco et al. |
| 7,400,055 B2 | 7/2008 | Nagao |
| 7,488,392 B2 | 2/2009 | Benum et al. |
| 7,491,376 B2 | 2/2009 | Barron et al. |
| 7,718,221 B2 | 5/2010 | Budaragin et al. |
| 2001/0003010 A1 | 6/2001 | Pham et al. |
| 2002/0004028 A1 | 1/2002 | Margrave et al. |
| 2002/0006470 A1 | 1/2002 | Eberspacher et al. |
| 2002/0041928 A1 | 4/2002 | Budaragin |
| 2002/0182468 A1 | 12/2002 | Janousek et al. |
| 2002/0187091 A1 | 12/2002 | Deevi |
| 2004/0033319 A1 | 2/2004 | Yamada et al. |
| 2004/0061114 A1 | 4/2004 | Yan et al. |
| 2004/0188323 A1 | 9/2004 | Tzatzov et al. |
| 2005/0089684 A1 | 4/2005 | Barron et al. |
| 2005/0201919 A1 | 9/2005 | Yu et al. |
| 2005/0247339 A1 | 11/2005 | Barnham et al. |
| 2005/0257744 A1 | 11/2005 | Boardman et al. |
| 2005/0257857 A1 | 11/2005 | Benum et al. |
| 2005/0277024 A1 | 12/2005 | West et al. |

(56) References Cited

U.S. PATENT DOCUMENTS

| | | | |
|---|---|---|---|
| 2006/0024547 A1 | 2/2006 | Waldbillig et al. | |
| 2006/0035130 A1 | 2/2006 | Noda et al. | |
| 2006/0040168 A1 | 2/2006 | Sridhar | |
| 2006/0063052 A1 | 3/2006 | Hu et al. | |
| 2006/0196419 A1 | 9/2006 | Tudhope et al. | |
| 2006/0198965 A1 | 9/2006 | Tudhope et al. | |
| 2006/0199057 A1* | 9/2006 | Hiwatashi | 429/30 |
| 2006/0231549 A1 | 10/2006 | Kisner | |
| 2007/0015002 A1 | 1/2007 | Narula et al. | |
| 2007/0059576 A1* | 3/2007 | Jacobson et al. | 429/31 |
| 2007/0077440 A1 | 4/2007 | Gawalt | |
| 2007/0184322 A1* | 8/2007 | Huang et al. | 429/32 |
| 2007/0227120 A1 | 10/2007 | Yodice et al. | |
| 2007/0237998 A1 | 10/2007 | Armstrong et al. | |
| 2007/0262059 A1 | 11/2007 | Boardman et al. | |
| 2008/0029494 A1 | 2/2008 | Tudhope et al. | |
| 2008/0063587 A1 | 3/2008 | Strano et al. | |
| 2008/0118777 A1 | 5/2008 | Li et al. | |
| 2008/0131749 A1 | 6/2008 | Hilliard | |
| 2008/0318092 A1 | 12/2008 | Sridhar et al. | |
| 2009/0098289 A1 | 4/2009 | Deininger et al. | |

FOREIGN PATENT DOCUMENTS

| | | | |
|---|---|---|---|
| EP | 97/682696 B1 | 12/1997 | |
| EP | 01/1088908 A2 | 4/2001 | |
| FR | 2617507 | 1/1989 | |
| GB | 1049428 | 11/1966 | |
| SU | 923232 A1 | 7/1980 | |
| WO | 85/00997 | 3/1985 | |
| WO | 92/10651 | 6/1992 | |
| WO | 94/18299 | 8/1994 | |
| WO | 97/25146 | 7/1997 | |
| WO | 02/14657 A1 | 2/2002 | |
| WO | 03/021004 | 3/2003 | |
| WO | 03/070640 | 8/2003 | |
| WO | 2004/104261 A1 | 12/2004 | |
| WO | 2005/019324 | 3/2005 | |
| WO | 2005/035951 A1 | 4/2005 | |
| WO | 2007/009104 | 1/2007 | |
| WO | 2008/123484 | 10/2008 | |
| WO | 2008-123484 A1 | 10/2008 | |
| WO | 2008/130433 | 10/2008 | |
| WO | 2009/126875 A2 | 10/2009 | |
| WO | 2009/129380 A2 | 10/2009 | |
| WO | 2011/100361 A2 | 8/2011 | |
| WO | 2011-100361 A2 | 8/2011 | |

OTHER PUBLICATIONS

Hampikian, J.M., Carter, W.B., The combustion chemical vapor deposition of high temperature materials, Materials Science and Engineering A267 (1999) pp. 7-18.*
Notes, "ASM Fuel Cell Overview," (Oct. 2003) by Paul Fisher (2 pages).
Notes, "Fuel Cells 2004," (May 2004) by Paul Fisher (7 pages).
Notes, "CAMP/Nano-Network," (Jun. 2004) by Paul Fisher (2 pages).
Notes, "ASM/Columbus, OH," (Oct. 2004) by Paul Fisher (3 pages).
Notes, "Feb. 7, 2007," (Jul. 2007) by Paul Fisher (25 pages).
Notes, "Notes on Advances in SOFCs II," (Dec. 2007) by Paul Fisher (9 pages) (referencing "Advances in Solid Oxide Fuel Cells II," (N.P. Bansal et al., Eds., John Wiley & Sons 2007)).
Sandrine Colson-Inam, "Solid Oxide Fuel Cells Ready to Market?" FuelCellToday.com (Jan. 2004).
Sylvia Baron, "Intermediate Temperature (500-850) SOFC's Explained," FuelCellToday.com (Jan. 2004).
Gregor Knoner et al., "Enhanced oxygen diffusivity in interfaces of nanoctystalline ZrO2.Y2O3," PNAS vol. 100 No. 7, 3870-73 (Apr. 2003).
Matthew Seabaugh, Ph.D. et al., "Tailor Made," Ceramic Industry 24-27 (Apr. 2007).

"Development of a Portable Solid Oxide Fuel Cell," NanoDynamics, Inc. Presentation (May 2004).
William Smith, "Regenerative Fuel Cells for Renewable Energy Storage," Presentation (May 2004).
Zhenguo G. Yang et al., "Solid Oxide Fuel Cells, Materials for the Bipolar Plates of SOFC," Advanced Materials & Processes, 34-37 (Jun. 2003).
N. P. Brandon et al., "Development of Metal supported Solid Oxide Fuel Cells for Operation at 500-600 degrees celsius," Journal of Materials vol. 13, 253-56 (Jun. 2004).
Dillon D. Fong et al., "Ferroelectricity in Ultrathin Perovskite Films," Science vol. 304, 1650-53 (Jun. 2004).
"Revolution, Mobile, Powerful," Electrical Contractor 5-7 (Jun. 2004).
Zongping Shao et al., "A thermally self-sustained micro solid-oxide fuel-cell stack with high power density," Nature, 795-98 (Jun. 2005).
Emmeline Chen, "Solid-Oxide Fuel Cells Stack Up to Efficient Clean Power," Research Highlights, S&TR, 17-19 (Sep. 2002).
Material Solutions Conference Final Program, pp. 37, 65-67 (Oct. 2003).
Steven G. Chalk and S. R. Venkateswaran, "Is there a Continuing Role for the Federal Government in Fuel Cell R&D for Transportation?" 1998 Fuel Cell Seminar (Nov. 1998).
W.N. Lawless, "Honeycomb Fuel Cell," CeramPhysics. Inc. (Nov. 2003).
"World's Highest Efficiency for 1kW Class Power Generation," Kyocera (Dec. 2003) (accessed at http://global.kyocera.com/news/2003/1205.html on Aug. 2, 2006).
K. Muthukkumaran et al., "Ionic Conductivity Measurements in Gadolinia Doped Ceria," Int. Symp. Res. Students Mater. Sci. Eng. (Dec. 2004).
K. Huang, "Oxide-ion conducting ceramics for solid oxide fuel cells," Journal of Material Science, vol. 36, 1093-1098 (2001).
V. V. Kharton et al., "Ceria-Based Materials for Solid Fuel Cells," Journal of Materials Science, vol. 36, 1105-1117, (2001).
"Fuel Cells for Building and Vehicles," ORNL Review vol. 35 No. 2 (2002).
Austin Weber, "Fuel Cells Fact Not Fiction," Assembly 70-77 (2003).
"Cool fuel cells could revolutionize Earth's energy resources," Nanodynamics, Inc. (2004).
"Can gold be employed as a fuel cell catalyst," Catgold Issue No. 8, 3 (2005).
Michael Hill, "Material Trends in SOFC Systems," Ceramic Industry/Ceramic Energy 6-8 (2005).
Igor Kosacki, "Nanoscaled Oxide Thin Films for Energy Conversion," NATO Science Series II, 1-18 (2005).
E. Koep el al., "Microstructure & Electrochemical Properties" J. Power Sources 161, 250-255 (2006).
D. Todorovsky et al., "Spray-Pyrolysis, Deep and Spin-Coating Deposition of Thin Films and Their Characterization," Journal of the University of Chemical Technology and Metallurgy, vol. 41, No. 1, 93-96 (2006).
Binod Kumar et al., "Electrical Properties of Heterogeneously Doped Yttria Stabilized Zirconia" (undated).
C. Bentley et al., "Direct Fuel Cell Commercialization," Fuel Cell Energy, Inc. (undated).
Eric Wachsman, "Fundamentals of Ionic Transport," High Temperature Electrochemistry Center (accessed at http://hitech.mse.ufl.edu/Wachsman%201.htm on Jun. 23, 2006).
Henry Petroski, "Fuel Cells," American Scientist, vol. 91, 398-402 (2003).
Igor Kosacki et al., "Surface Interface-Related Conductivity in Nanometer Thick YSZ Films," Electrochemical and Solid-State Letters, 7, (12) A459-A461 (2004).
John Halloran et al., "Redefining Ceramic Fuel Cells," Ceramic Industry 25-28 (Apr. 2008).
E. Lara-Curzio "Mechanical Properties of tape cast nickel-based anode materials for solid oxide fuel cells before and after reduction in hydrogen," Acta. Mater. vol. 52 5747-5756 (2004).
"PAD: Polymer-Assisted Deposition of Metal-Oxide Films," Los Alamos National Laboratory (2006).
Maria Mercedes Gonzalez-Cuenca, Dissertation "Novel Anode Materials for Solid Oxide Fuel Cells" (2002).

(56) References Cited

OTHER PUBLICATIONS

Katsuyo Thornton et al.,"Nanotechnology for Fuel Cells and Batteries," NSF Workshop; Section 4 (accessed at www.cs.duke.edu . . . on Mar. 1, 2007.).

"Solid Oxide Fuel Cell Compositions," Praxair (accessed at www.praxair.com on Sep. 14, 2006).

"New Metal-Oxide Process," Semiconductor International (2005) (accessed at www.reed-electronics.com on Jun. 29, 2007).

S. Kang et al., "Thin-Film Solid Oxide Fuel Cells on Porous Nickel Substrates with Multistage Nanohole Array," Journal of the Electrochemical Society, 153 (3) A554-A559 (2006).

Sol Gel Technology, (accessed at www.chemat.com/html/solgel.html on Nov. 7, 2003).

Tatsumi Ishihara et al., "Electrolytes," in High Temperature Solid Oxide Fuel Cells, Fundamentals, Design and Applications, Chapter 4, Elsevier (2003).

"Solid Oxide Fuel Cell," Wikipedia.org (accessed Oct. 3, 2007).

International Preliminary Report on Patentability, PCT/US2011/024242 (published as WO 2011-100361), dated Aug. 14, 2012 (5 pages).

K. An, "Mechanical Properties and Electrochemical Durability of Solid Oxide Fuel Cells," Ph.D. Dissertation, Virginia Polytechnic Institute and State University (2003).

A. Krishnan, "Solid Oxide Membrane Process for the Direct Reduction of Magnesium from Magnesium Oxide," Ph. D. Dissertation, Boston University (2006).

Fujishima et al., 70 Pure Appl. Chem. (1998) 2177-87.

S. Hofmann, "Gold catalyzed growth of silicon nanowires by plasma enhanced chemical vapor deposition," Journal of Applied Physics vol. 94, No. 9 (2003).

Rosnita Muhammad, Zulkafli Othaman, Samsudi Sakrani Yussof Wahab, "Vapor-liquid solid mechanism using gold colloids for the growth of GaAs nanowires," Physics Department, Faculty of Science, Universiti Teknologi Malaysia, 81310 UTM, Skudai, Johor (2008).

Igor Kosacki, Toshio Suzuki, Harlan U. Anderson, Philippe Colomban, "Raman scattering and lattice defects in nanocrystalline $CeO_2$ thin films," Solid State Ionics 149 (2002) 99-105.

J. Britt, Photovoltaic Manufacturing Cost and Throughput Improvements for Thin Film CIGS-Based Molecules: Final Technical Report, Apr. 2002, National Renewable Energy Laboratories.

English-language abstract for SU 923232 A1 Filippov et al.

R. Goettler, "Overview of the Rolls-Royce SOFC Technology and SECA Program," Jul. 14, 2009.

G.C. Hood et al., "Aluminum Acetates and Propionates—Their Preparation and Composition," 72 J. Am. Chem. Soc., 2094-95 (1950).

Narayanan et al., "Synthesis of Soluble Aluminium Carboxylates Directly from Aluminium Hydroxide," J. Mater. Chem., 10 (2000) 2097-104.

M. Brown, "Taking the Heat," Frontiers (Apr. 2004) pp. 34-37.

Written Opinion for PCT/US2011/024242 dated Oct. 28, 2011.

Hernadi et al., "Synthesis of MWNT-based Composite Materials with Inorganic Coating," 51 Acta Materialia (2003) pp. 1447-1452.

Garcia-Barriocanal et al., Colossal Ionic Conductivity at Interfaces of Epitaxial $ZrO_2$:$Y_2O_3$/$SrTiO_3$ Heterostructures, 321 Science 676 (2008).

Chen et al., "Photocatalytic Degradation of Methylene Blue by CNT/$TiO_2$ Composites Prepared from MWCNT and Titanium n-Butoxide with Benzene," 45 J. Korean Ceram. Soc. (2008) 651-57.

Zhu et al., "Preparation and Characterization of New Photocatalyst Combined MWCNTs with $TiO_2$ Nanotubes," 17 Trans. Nonferrous Met. Soc. China (2007) s1117-s1121.

Latu-Romain et al., "Growth Parameters and Shape Specific Synthesis of Silicon Nanowires by the VLS Method," 10 J. Nanopart Res. (2008) 1287-91.

Civale et al., "Aspects of Silicon Nanowire Synthesis by Aluminum-Catalyzed Vapor-Liquid-Solid Mechanism," Proceedings of 7th Annual Workshop on Semiconductor Advances for Future Electronics (SAFE 2004), Nov. 25-26, 2004, Veldhoven, The Netherlands,Publ. STW, ISBN 90-73461-43-X, pp. 692-696.

Kanai et al., "Semiconductor Testing Probe Utilizing Silicon Whisker Grown by VLS (Vapor Liquid Solid) Method," Tokyo Cathode Laboratory (Jun. 6, 2001) (available at: http://www.swtest.org/swtw_library/2001proc/PDF/S7_01.pdf (accessed Feb. 20, 2009).

Hu et al., "$TiO_2$ Thin Films Prepared from Aqueous Solution and Their Sterilizing Capability," 7 J. Ceram. Proc. Res., (2006) 49-52.

Final Office Action dated Oct. 23, 2008 in U.S. Appl. No. 10/440,802 (Now U.S. Pat. No. 7,718,221), Budaragin et al, May 18, 2010.

"Zirconia Toughened Alumina ZTA—Properties and Applications of ZTA by Dynamic Ceramic Ltd." (available at http://www.azom.com/details.asp?ArticleID=3303)(accessed Dec. 7, 2007).

"High Emissivity Coating Technology Improves Heater Performance" (available at http://www.cisoilgas.com)(2012) (accessed May 30, 2012).

Report description and table of contents, "Curtailing Coke Formation in Ethylene Furnace Tubes" Nexant, Inc., Jun. 4, 2003 (available at http://nexant.ecnext.com/coms2/gi_0255-146/Curtaining-Coke-Formation-in-Ethylene.html (accessed Sep. 27, 2007).

Zervos et al., "Printed and Thin Film Photovoltaics and Batteries," (IDTechEx, Jun. 2008) (available at http://www.idtechex.com/research/reports/printed_and_thin_film_photovoltaics_and_batteries_000172.asp) (accessed Mar. 5, 2009).

Z.L. Wang, T.S. Ahmad and M.A. El-Sayed, "Steps, Ledges and kinks on the surfaces of platinum nanoparticles of different shapes," Surface Science, 380,302 (1997).

G. Rupprechter, K. Hayek and H. Hofmeister, "Electron microscopy of thin-film model catalysts: activation of alumina-supported rhodium nanoparticles, "Journal of Catalysts, 173, 409 (1998).

Zhong Lin Wang and Xiangdong Feng, "Polyhedral shapes of $CeO_2$ nanoparticles," J. Phys. Chem. B, 107, 13563-66 (2003).

Roberet Schlogl and Shaifah Bee Abd Hamid, "Nanocatalysts: Mature Science Revisited or Something Really New?," Angew. Chem. Int. Ed., 43, 1628 (2004).

M. Adlim, Mohamad Abu Bakar, Kong Yong Liew and Jamil Ismail, "Synthesis of chitosan-stabilized platinum and palladium nanoparticles and their hydrogenation activity," Journal of Molecular Catalysis A, 212, 141 (2004).

V.K. Kapur, A. Bansal, O. I. Asensio, P. Le and N. K. Shigeoka, "Fabrication of CIGS Solar Cell via Printing of Nanoparticle Precursor Inks," International Solar Electric Technology Inc. (ISET) (2004).

Non-Final Office Action in U.S. Appl. No. 13/578,195, dated Nov. 7, 2013 (12 pages).

G.S. Chai et al., "Synthesis of Ordered, Uniform, Macroporous Carbons with Mesoporous Walls Templated by Aggregates of Polystyrene Spheres and Silica Particles for Use as Catalyst Supports in Direct Methanol Fuel Cells," Adv. Mater. 2004, 16, No. 22, 2057-2061.

G. Van De Goor et al., "Chromophore-Zeotype Composites: Direct Synthesis of an Array of Strictly Aligned Metal-Organic Complex Chromophores in a Crystalline Silica Matrix," Adv. Mater. 1996, 8, No. 1, 65-69.

* cited by examiner

SOLID OXIDE FUEL CELLS, ELECTROLYZERS, AND SENSORS, AND METHODS OF MAKING AND USING THE SAME

CROSS-REFERENCE TO RELATED APPLICATIONS

The present application claims benefit of priority under 35 U.S.C. §119(e) to U.S. Provisional Patent Application No. 61/043,566 entitled, "Solid Oxide Fuel Cells, Electrolyzers, and Sensors, and Methods of Making and Using the Same" filed on Apr. 9, 2008, which is incorporated herein by reference in its entirety.

FIELD OF THE INVENTION

The present invention relates to electrical energy systems such as fuel cells, electrolyzer cells, and sensors, and, in particular, to solid oxide fuel cells, solid oxide electrolyzer cells, solid oxide sensors, and components of any of the foregoing.

BACKGROUND OF THE INVENTION

Solid oxide fuel cells, otherwise known as ceramic fuel cells, present an environmentally friendly alternative to mainstream electrical energy production processes involving the combustion of fossil fuels. Solid oxide fuel cells enable the catalytic conversion of chemical energy stored in hydrogen into electrical energy without the concomitant release of greenhouse gases. The generation of electrical current by a solid oxide fuel cell using a hydrogen fuel results in the production of water as opposed to the production carbon dioxide, nitrous oxides, and/or sulfur dioxides associated with the combustion of fossil fuels.

In addition to hydrogen, solid oxide fuel cells are operable to function on a wide variety of fuel sources. Fuel sources in addition to hydrogen include hydrocarbons such as methane, natural gas, and diesel fuel. Hydrocarbon fuel sources are reformed into hydrogen for use with solid oxide fuel cells. Hydrocarbon reforming can be administered prior to entry into the fuel electrode or can be administered at the fuel electrode of a solid oxide fuel cell. The ability to function on a wide variety of fuels distinguishes solid oxide fuel cells from other fuel cells which lack the ability to operate on various fuels. Furthermore, the ability of solid oxide fuel cells to administer hydrocarbon feedstock reformation frees such fuel cells from the limitations associated with hydrogen production and distribution.

Currently, solid oxide fuel cells operate at high temperatures ranging from about 800° C. to 1000° C. As a result of high operating temperatures, solid oxide fuel cells require the use of exotic materials which can withstand such operating temperatures. The need for exotic materials greatly increases the costs of solid oxide fuel cells, making their use in certain applications cost-prohibitive. Moreover, high operating temperatures often induce grain growth in the various component layers of a solid oxide fuel cell, including the electrolyte. Grain growth can reduce ion conductivity through the electrolyte thereby degrading the efficiency of the solid oxide fuel cell. High operating temperatures additionally exacerbate stresses caused by differences in coefficients of thermal expansion between component layers of a solid oxide fuel cell. Differences in coefficients of thermal expansion between component layers of a solid oxide fuel cell can lead to cracking at interfaces of the layers as well as within the layers. Differences in coefficients of thermal expansion between the air electrode and the electrolyte, for example, can lead to cracking at the electrode-electrolyte interface and within the electrode and/or electrolyte.

In certain circumstances, a solid oxide fuel cell can operate "in reverse" to electrolyze water into hydrogen gas and oxygen gas by inputting electrical energy. In other circumstances, a solid oxide electrolyzer cell can be designed primarily for use as a hydrolyzer, generating hydrogen and oxygen for later use. In still other circumstances, an electrolyzer cell can be used for other purposes, such as extraction of metal from ore and electroplating. In conventional electrolyzers, electrical energy is lost in the electrolysis reaction driving the diffusion of ions through the electrolyte and across the distance between the electrodes. Also, the ability to conduct electrolysis at higher temperatures would improve the efficiency of the electrolysis. However, at higher temperatures, electrolyzers face similar thermal stresses and cracking caused by differences in coefficients of thermal expansion between component layers of the solid oxide electrolyzer cell. Accordingly, better matching of coefficients of thermal expansion is desired for electrolyzer cells.

A lambda sensor is a device typically placed in the exhaust stream of an internal combustion engine to measure the concentration of oxygen. That measurement allows regulation of the richness or leanness of the fuel/air mixture flowing into the engine. If the fuel/air stream contains too much oxygen, the quantity $\lambda$ is greater than 1, and the mixture is too lean. If the fuel/air stream contains too little oxygen, then $\lambda<1$ and the mixture is too rich. $\lambda$ equals 1, the ideal situation, when the mixture contains a stoichiometrically equivalent concentration of oxygen and hydrocarbon to allow for complete combustion. A lambda sensor positioned in the exhaust stream detects the amount of oxygen in the combustion products, thereby providing feedback regarding richness or leanness. Lambda sensors and other sensors rely on the diffusion of oxygen anions ($O^{2-}$) and other ions through barrier materials in ways similar to the manner in which oxygen anions diffuse through a solid electrolyte of a solid oxide fuel cell. Moreover, given the high operating temperature of lambda sensors and similar devices, sensors face thermal stresses, cracking, and delamination issues similar to those facing fuel cells and electrolyzers. Accordingly, embodiments of the present invention provide for improved sensor technology by addressing mismatching of coefficients of thermal expansion, among other reasons.

SUMMARY

In view of the foregoing problems and disadvantages associated with the high operating temperatures of solid oxide cells, it would be desirable to provide solid oxide cells that can demonstrate lower operating temperatures. In addition, providing solid oxide cells and components that better tolerate higher temperatures would be advantageous. Moreover, the efficiency losses due to the thickness of electrolytes make thinner electrolytes desirable.

As used herein, "solid oxide cell" means any electrochemical cell that contains at least one metal oxide, and refers to, for example, solid oxide fuel cells, solid oxide electrolyzer cells, cells that can operate as a fuel cell and an electrolyzer cell, and solid oxide sensors.

One method of lowering operating temperatures of solid oxide cells is to increase the efficiency of oxygen transport across the solid electrolyte. Since oxygen transport efficiency decreases linearly with electrolyte thickness, the thinner the electrolyte layer, the higher the efficiency of oxygen transport. Thus, the thinner the electrolyte, the higher the operating efficiency of the solid oxide cell will be. A thinner electrolyte layer also can lower the operating temperature of a solid oxide cell.

Some embodiments of the present invention provide electrolyte in the form of an ultra-thin yet fully dense film having a thickness less than 1 micron. A thickness less than 1 µm represents a reduction in thickness of 2-3 orders of magnitude over many existing ceramic electrolyte constructions.

In addition, by lowering the operating temperature of a solid oxide cell, less exotic and easier-to-fabricate materials can be utilized in the construction of the cell leading to lower production costs. Thus, some embodiments of the present invention provide solid oxide cells and components thereof employing simpler, less-expensive materials than the current state of the art. For example, if the operating temperature of a solid oxide cell can be lowered, then metals can be used for many different components such as electrodes and interconnects. At these lower operating temperatures, metals have more desirable mechanical properties, such as higher strength, than ceramics. In addition, this higher strength can allow metal components also to have a higher degree of porosity. Current ceramic electrode materials allow for porosity levels in the range of 30% to 40%. Incorporating higher porosity levels in ceramic materials renders them too structurally weak to support cell construction. However, through the use of certain metals or metal carbides, the porosity of an electrode can be provided in the higher range of 40% to 80% and yet retain sufficient mechanical strength for cell construction. Some embodiments of the present invention provide an electrode having a porosity ranging from about 40% to about 80%.

Lower production costs in addition to lower operating temperatures provide the opportunity for solid oxide cells to find application in a wider variety of fields. Additionally, lower operating temperatures reduce degradative processes such as those associated with grain growth and variances in coefficients of thermal expansion between dissimilar component layers of the cell. Accordingly, some embodiments provide means and methods for reducing at least one degradation process in a solid oxide cell.

Further embodiments of the present invention apply conformal nano-scale surface treatments to porous metal substrates so that the pore size can be reduced to either micron- or submicron-dimensions; thus, the increase in the active surface area of an electrode component results in an increase in the efficiency of the electrode by as much as an order of magnitude.

Still other embodiments produce a desirable surface catalytic effect. For example, by using a process of some embodiments of the present invention, thin films of metal oxides and pure metals (or other metal compounds) can be formed on the exposed pore surfaces of electrodes to produce more chemically active sites at triple phase boundaries where either fuel-gas (as in the case of the anode electrode) or gaseous oxygen (as in the case of the cathode electrode) come into contact with the solid (yet porous) electrodes in a fuel cell.

Other embodiments provide methods of making solid oxide cells and components thereof. Current methods of making solid oxide fuel cells involve the sintering of ceramic and/or metal powders. High sintering temperatures during fabrication of various components, such as the electrolyte, can result in excessive grain growth as well as compound problems associated with variances in coefficients of thermal expansion. Furthermore, sintering provides little control over the ability to vary the composition of an electrolyte or electrode as a function of the thickness of the electrolyte or electrode.

In one embodiment, the present invention provides a solid oxide fuel cell comprising an air electrode, a fuel electrode, an electrolyte interposed between the air electrode and the fuel electrode, and at least one electrode-electrolyte transition layer. In other embodiments of the present invention, an electrode-electrolyte transition layer is interposed between an electrode and the electrolyte. An electrode-electrolyte transition layer, in some embodiments, is interposed between the air electrode and the electrolyte. In other embodiments, an electrode-electrolyte transition layer is interposed between the fuel electrode and the electrolyte. In a further embodiment, a solid oxide fuel cell comprises a first electrode-electrolyte transition layer interposed between the air electrode and electrolyte and a second electrode-electrolyte transition layer interposed between the fuel electrode and the electrolyte. In one embodiment, a solid oxide fuel cell does not comprise an electrode-electrolyte transition layer, and an abrupt interface exists between an electrode and electrolyte. Even other embodiments provide more than one electrode-electrolyte transition layer.

Moreover, in order to reduce problems and disadvantages associated with variances in coefficients of thermal expansion between electrodes and electrolytes of solid oxide cells and to increase ionic conductivities, electrolytes of certain embodiments of the present invention comprise compositional gradients. An electrolyte of a solid oxide cell, in one embodiment, comprises a region proximal to an electrode and a region distal to the electrode, wherein the region proximal to the electrode comprises a greater amount of electrode material than the region distal to the electrode. An electrode, for example, comprises $La_{1-x}Sr_xMnO_3$ [lanthanum strontium doped manganite (LSM)]. The region of the electrolyte proximal to the electrode comprises greater amounts of LSM in comparison with the region of the electrolyte distal from the electrode.

An electrolyte of a solid oxide cell, in another embodiment, comprises a plurality of metal oxide layers. Metal oxide layers of the electrolyte proximal to an electrode comprise a greater amount of electrode material than metal oxide layers of the electrolyte distal to the electrode. An electrode, for example, comprises $La_{1-x}Sr_xMnO_3$ [lanthanum strontium doped manganite (LSM)]. Metal oxide layers of an electrolyte proximal to the electrode, in one embodiment, comprise greater amounts of LSM in comparison with metal oxide layers of the electrolyte distal from the electrode.

Incorporating greater amounts of electrode material in an electrolyte region or electrolyte layers proximal or adjacent to the electrode in a solid oxide cell establishes a compositional gradient in the electrolyte. Such a compositional gradient can permit an electrolyte region or electrolyte layers proximal to the electrode to demonstrate a coefficient of thermal expansion which better matches the coefficient of thermal expansion of the electrode. As a result, disparities in coefficients of thermal expansion between the electrode and the electrolyte can be reduced or eliminated leading to a more stable solid oxide cell.

In view of this, in some embodiments, a solid oxide cell comprises a first electrode comprising a first material and an electrolyte comprising a first region proximal to the first electrode and a second region distal to the first electrode, wherein the first region of the electrolyte comprises a greater amount of the first material than the second region of the electrolyte.

In another embodiment, a solid oxide cell comprises a first electrode comprising a first material and an electrolyte comprising a plurality of layers of an electrolyte material, wherein layers of the electrolyte material proximal or adjacent to the first electrode further comprise greater amounts of the first material of the first electrode than layers of the electrolyte distal or spaced apart from the first electrode.

In order to reduce problems and disadvantages associated with variances in coefficients of thermal expansion between electrode and electrolytes of solid oxide cells, electrodes, in some embodiments of the present invention, comprise compositional gradients. An electrode, in one embodiment, comprises a region proximal to the electrolyte and a region distal to the electrolyte, wherein the region proximal to the electrolyte comprises a greater amount of electrolyte material than the region of the electrode distal to the electrolyte. In another embodiment, an electrode of a solid oxide cell comprises a plurality of layers. Layers of the electrode proximal to the electrolyte comprise greater amounts of electrolyte material than layers of the electrode distal to the electrolyte. A solid oxide cell, in some embodiments, comprises a first electrode comprising a plurality of layers of a first material and an electrolyte comprising an electrolyte material disposed on the first electrode, wherein layers of the first material proximal or adjacent to the electrolyte further comprise greater amounts of the electrolyte material than layers of the first material distal or spaced apart from the electrolyte.

In addition to variances in coefficients of thermal expansion, some of the solid oxide cells of the present invention also address fuel, air, and other reactant delivery mechanisms by providing electrodes comprising porosity and optionally, porosity gradients. For example, electrodes of solid oxide fuel cells may be porous in order to allow the ingress of air and fuel to the electrolyte and the egress of other gases produced or not consumed by the fuel cell. In one embodiment, a solid oxide cell comprises a solid electrolyte disposed on a first electrode, the first electrode comprising a first region proximal to the solid electrolyte and a second region distal to the electrolyte, wherein the first region has a porosity less than the second region. Alternatively, in another embodiment, the first region of the electrode has a porosity that is greater than the second region of the electrode. One embodiment provides a porous electrode having a first region adapted to be proximate to electrolyte having pores of approximately 200 nm in diameter, and a second region adapted to be distal to the electrolyte having pores of approximately 10-15 µm in diameter. The two regions can be any suitable thickness. For example, the first region can be 200 nm thick, and the second region can be about 1 µm thick. The thicknesses of the two (or more, if desired) regions balance the mechanical strength of the porous electrode with the movement of reactant and product gases through the electrode. If the electrode is too thin, then it may be too brittle. If it is too thick, movement of gas through the electrode may hinder cell operation.

Moreover, in some embodiments, a solid oxide cell comprises a first electrode comprising a plurality of layers of a first material and a solid electrolyte disposed on the first electrode, wherein layers of the first material proximal to the solid electrolyte have porosities less than layers of the first material distal to the solid electrolyte. Alternatively, in other embodiments, layers of the first material proximal to the solid electrolyte have porosities greater than layers of the first material distal to the solid electrolyte.

In another aspect, some embodiments of the present invention provide electrodes operable in solid oxide cells as well as other applications. Electrodes of the present invention, in some embodiments, are resistant to harsh environments and various chemical species which can foul the electrodes, such as sulfur. In one embodiment, the present invention provides an electrode comprising a substrate comprising a first material, a coating comprising at least one layer of at least one metal oxide disposed on the substrate, and a substrate-coating transition layer interposed between the substrate and the coating. As used herein, "diSposed on the substrate" need not mean, for example, that the at least one layer of at least one metal oxide directly contacts the substrate. Moreover, "interposed between the substrate and the coating" does not necessarily mean that the transition layer is inserted between the substrate and the coating after the coating is formed. Forming those embodiments is described in more detail below. In some embodiments, an electrode comprises a plurality of layers of at least one metal oxide disposed on the substrate. An electrode, in one embodiment, is an anode. An electrode, in another embodiment, is a cathode. In some embodiments, the metal oxide coating of an electrode can protect the electrode substrate from corrosion and/or degradation.

Electrodes, according to some embodiments, further comprise at least one catalytic material. Catalytic materials can comprise transition metals including, but not limited to, platinum, palladium, rhodium, nickel, cerium, gold, silver, zinc, lead, ruthenium, rhenium, or mixtures thereof. Catalytic materials, in some embodiments, are disposed in one or a plurality of metal oxide layers coating the substrate. The combination of a metal oxide with pure metals or alloys, in some embodiments, produces a cermet. Electrodes of solid oxide fuel cells further comprising catalytic materials can function as fuel reformers converting hydrocarbon fuels into hydrogen for subsequent use in the solid oxide fuel cell. Moreover, electrodes further comprising catalytic materials can function as fuel reformers upstream and independent from solid oxide fuel cells.

Electrodes comprising catalytic materials can optionally demonstrate compositional gradients based on the distribution of the catalytic materials in the plurality of metal oxide layers. In one embodiment, an electrode comprises a substrate and a plurality of metal oxide layers disposed on the substrate, wherein metal oxide layers proximal to the substrate comprise greater amounts of catalytic material than metal oxide layers distal to the substrate. Moreover, in another embodiment, metal oxide layers distal to the substrate comprise greater amounts of catalytic material than metal oxide layers proximal to the substrate.

In another aspect, the present invention provides interconnects operable to be used in solid oxide cells as well as other applications. Interconnects of the present invention, in some embodiments, are resistant to harsh environments and chemical species which can degrade the interconnects. In one embodiment, the present invention provides an interconnect comprising a substrate comprising a first material, a coating composition comprising at least one layer of metal oxide, and a substrate-coating transition layer interposed between the substrate and the coating. In some embodiments, a coating composition comprises a plurality of metal oxide layers. One or a plurality of metal oxide coatings can assist in protecting a metallic or ceramic interconnect substrate from degradative conditions and/or chemical species.

Additionally, in order to reduce problems and disadvantages associated with variances in coefficients of thermal expansion between interconnects and electrodes of solid oxide cells, interconnects, in some embodiments of the present invention, comprise one or more compositional gradients. An interconnect, in one embodiment, comprises a region proximal to a cathode of a solid oxide cell and a region distal to the cathode, wherein the region proximal to the cathode has a greater amount of cathode material than the region of the interconnect distal from the cathode. Moreover, in another embodiment, an interconnect comprises a region proximal to an anode of a solid oxide cell and a region distal to the anode, wherein the region proximal to the anode has a greater amount of anode material than the region of the interconnect distal from the anode.

In another embodiment, an interconnect comprises a substrate coated with a plurality of metal oxide layers. Layers of the interconnect proximal to the cathode comprise greater amounts of cathode material than layers of the interconnect distal from the cathode. Moreover, in another embodiment, layers of the interconnect proximal to the anode comprise greater amounts of anode material than layers of the interconnect distal from the anode.

Some embodiments of the present invention provide materials in which more than one concentration gradient is present. For example, in a material A between two other materials B and C, the material A can exhibit one independent concentration gradient of the material B, and a second independent concentration gradient of material C. Gradients of various other ingredients and properties, such as porosity, also can be exhibited in those and other embodiments of the present invention. Such independent gradients can be formed, in some embodiments, by successive disposition of layers of material A, wherein each successive layer contains the desired amount of material B, material C, and porosity, for example.

In another aspect, the present invention provides methods of making solid oxide cells. In one embodiment, a method of making a solid oxide cell comprises providing a first electrode, applying a metal compound composition to the first electrode, and converting at least some of the metal compound composition to a metal oxide composition. In some embodiments, the metal compound composition is fully converted to a metal oxide composition. In some embodiments, the metal compound composition comprises at least one metal carboxylate, at least one metal alkoxide, at least one metal β-diketonate, or a combination thereof.

Converting a metal compound composition, according to some embodiments of the present invention, comprises exposing the metal compound composition to an environment operable to convert the at least one metal salt to at least one metal oxide. Environments operable to convert metal compounds to metal oxides, in some embodiments, demonstrate conditions sufficient to vaporize and/or decompose the compounds and precipitate metal oxide formation. In one embodiment, an environment operable to convert metal compounds to metal oxides comprises a heated environment. A metal salt of a carboxylic acid, for example, can be exposed to an environment heated to a temperature operable to evaporate the carboxylic acid and induce formation of the metal oxide. In some embodiments, the environment is heated to a temperature greater than about 400° C. In other embodiments, the environment is heated to a temperature ranging from about 400° C. to about 650° C. In some embodiments, the environment is heated to a temperature of up to about 425° C. or up to about 450° C. In still other embodiments, the environment is heated to a temperature ranging from about 650° C. to about 800° C., or from about 800° C. to about 1000° C.

In some embodiments, an environment operable to convert metal compounds to metal oxides is free or substantially free of oxygen. In other embodiments, an environment operable to convert metal compounds to metal oxides comprises oxygen.

In another embodiment, a method of making a solid oxide cell comprises providing a first electrode and depositing at least one electrolyte layer on the first electrode, wherein depositing at least one electrolyte layer comprises applying a metal compound composition to the first electrode, and converting at least some of the metal compound composition to at least one metal oxide.

In some embodiments, a plurality of electrolyte layers is stacked on the first electrode. A method of producing a solid oxide cell, in one embodiment, comprises providing a first electrode and stacking a plurality of electrolyte layers on the first electrode, wherein each layer of electrolyte is stacked on a preceding layer by applying a metal compound composition to the preceding layer. The metal compound composition is subsequently converted to at least one metal oxide.

In addition to solid oxide cells, the present invention provides methods of making electrodes. In one embodiment, a method of making an electrode comprises providing a substrate and depositing at least one metal oxide layer on the substrate wherein depositing comprises applying a metal compound composition to the substrate, and converting at least some of the metal compound composition to at least one solid oxide composition. In some embodiments, the metal compound composition is fully converted to a metal oxide.

In some embodiments, a plurality of metal oxide layers is deposited on the substrate. In one embodiment, for example, a method of making an electrode comprises depositing a plurality of metal oxide layers on the substrate, wherein each layer of metal oxide is deposited on a preceding layer by applying a metal compound composition to the preceding layer. The metal compound composition is subsequently converted to at least one metal oxide to form another layer of metal oxide.

Metal compound compositions, in some embodiments of electrode production methods, further comprise one or more catalytic materials. Catalytic materials, in such embodiments, comprise transition metals including, but not limited to, platinum, palladium, rhodium, nickel, cerium, gold, silver, zinc, lead, ruthenium, rhenium, or mixtures thereof. In other embodiments, metal compound compositions further comprise nanoparticles, powders, or both, operable to alter the pore structure and/or porosity of the metal oxide resulting from the conversion of the metal compound composition. Nanoparticles, in some embodiments, comprise metal oxide nanoparticles. Nanoparticles, as used herein, have an average size less than about 1 µm, while powders are those particulate materials having an average size equal to or greater than 1 µm.

In another aspect, the present invention provides methods of making interconnects. In one embodiment, a method of making an interconnect comprises providing a substrate and depositing at least one metal oxide layer on the substrate wherein depositing comprises applying metal compound composition to the substrate, and converting at least some of the metal compound composition to at least one metal oxide, thereby forming the at least one metal oxide layer. In some embodiments, the metal compound composition is fully converted to at least one metal oxide.

In some embodiments, a plurality of metal oxide layers are deposited on the substrate. In one embodiment, for example, a method of making an interconnect comprises depositing a plurality of metal oxide layers on the substrate, wherein each layer of metal oxide is deposited on a preceding layer by applying a metal compound composition to the preceding layer. The metal compound composition is subsequently converted to at least one metal oxide to form a layer.

In another aspect, the present invention provides methods of increasing the ionic conductivity of a solid electrolyte. A method of increasing the ionic conductivity of a solid electrolyte, in some embodiments, comprises increasing the number of grain boundaries in the solid electrolyte, wherein increasing the number of grain boundaries comprises forming a plurality of nanocrystalline grains comprising an electrolyte material. In some embodiments of the present invention, an electrolyte material comprises one or more metal oxides. Forming a plurality of metal oxide nanocrystalline grains comprises applying a metal compound composition to a substrate, and converting at least some of the metal compound composition to a plurality of metal oxide nanocrystalline grains.

In another aspect, the present invention provides methods of increasing the number of triple phase boundaries in a solid oxide cell comprising providing an electrolyte comprising a plurality of metal oxide nanocrystalline grains. Providing an electrolyte comprising a plurality of nanocrystalline grains, in some embodiments, comprises applying a metal compound composition to a substrate, and converting at least some of the metal compound composition to a plurality of metal oxide nanocrystalline grains. In some embodiments, the metal compound composition is fully converted into a plurality of metal oxide nanocrystalline grains. In one embodiment, the substrate comprises an electrode of a solid oxide cell.

In a further aspect, the present invention provides methods of reducing differences in coefficients of thermal expansion between an electrode and an electrolyte of a solid oxide cell. In one embodiment, a method of reducing differences in coefficients of thermal expansion between an electrode and an electrolyte comprises interposing an electrode-electrolyte transition layer between the electrode and the electrolyte. Interposing an electrode-electrolyte transition layer between the electrode and the electrolyte comprises applying an electrolyte composition comprising a metal compound composition to the electrode, and converting at least some of the liquid metal compound to at least one metal oxide.

In some embodiments of methods of the present invention, a metal compound comprises a transition metal compound. In other embodiments, a metal compound comprises a rare earth metal compound. In a further embodiment, metal compound compositions comprise a plurality of metal compounds. In one embodiment, a plurality of metal compounds comprises at least one rare earth metal compound and at least one transition metal compound. In still other embodiments, the at least one metal compound comprises metal ions that are the same or different, and ligands that are the same or different. In some embodiments, those ligands are chosen from one or more carboxylates, one or more alkoxides, one or more β-diketonates, and combinations thereof.

Moreover, in embodiments of methods of the present invention, metal compound compositions can comprise liquid metal compound compositions, solid metal compound compositions, vapor metal compound compositions, or combinations thereof. In one embodiment, a liquid metal carboxylate composition comprises an excess of the liquid carboxylic acid used to form the metal carboxylate salt. In another embodiment, a liquid metal compound composition comprises a solvent including, but not limited to, organic solvents such as benzene, toluene, xylene, chloroform, dichloromethane, or mixtures thereof. In some embodiments, solid metal compound compositions comprise metal compound powders. In a further embodiment, a vapor metal compound composition comprises at least one gas phase metal compound operable to condense on a substrate prior to conversion to at least one metal oxide. In one embodiment, a metal compound composition comprises at least one gel including, but not limited to, a sol-gel, hydrogel, or a combination thereof.

In yet another aspect, the present invention provides a method of generating electric current from a solid oxide fuel cell that comprises at least one air electrode (or cathode); at least one fuel electrode (or anode); and, at least one electrolyte layer interposed between the at least one air electrode and the at least one fuel electrode. This tri-layer construction, in some embodiments, also includes at least one electrode-electrolyte transition layer where fuel is in contact with the fuel electrode (or anode); and also, another electrode-electrolyte transition layer where gaseous oxygen is in contact with the air electrode (or cathode). The middle layer comprises the electrolyte, which can be solid, non-porous, and fully-dense. The middle electrolyte layer serves as a barrier that prevents premature mixing of the fuel gas (on the anode side of the cell) with the gaseous oxygen (on the cathode side of the cell). Other embodiments provide cells comprising more than one cathode electrode, and/or more than one anode electrode. Still other embodiments provide a plurality of cells, wherein the cells are connected in series, in parallel, or a combination thereof.

While not intending to be bound by theory, the solid oxide fuel cell of certain embodiments produces electricity as follows. Molecular diatomic oxygen is reduced to oxygen anions at the air electrode (or cathode). Diatomic hydrogen reacts with these oxygen anions after the oxygen anions have been transported through the electrolyte layer and to the anodic side of the tri-layer arrangement. When the hydrogen fuel and the oxygen anions form water, for example, as steam, electrons are also a product of this reaction. The electrons produced by the reaction can then flow around an external circuit (through an electrically-conductive interconnect). These electrons (released when water is formed) further become available for the repeated reduction of molecular diatomic oxygen into oxygen anions at the air electrode or cathode.

In this way, the production of both electric current and water is a continuous process—as long as hydrogen (from some hydrogen-containing fuel source) and oxygen continue to be supplied to the opposite sides of the cell (separated from each other by the electrolyte—as described above).

In some embodiments, the fuel comprises pure hydrogen. But, in other embodiments, the fuel comprises a hydrocarbon, such as a fossil fuel that contains hydrogen—but that also contains other elements such as carbon.

A solid oxide fuel cell has a unique ability among the various types of fuel cells to operate on either pure hydrogen or (with minor alterations) other types of fossil fuels and hydrocarbons. In embodiments wherein the fuel is a hydrocarbon, methods of generating electrical current further comprise "reforming" (or releasing hydrogen from hydrocarbon) the hydrocarbon fuel internally at the fuel electrode (or anode).

In another aspect, some embodiments provide a solid oxide electrolyzer cell or a component thereof comprising at least one metal oxide, wherein the at least one metal oxide has been made by a process comprising:
 applying at least one metal compound to a substrate, and
 converting at least some of the at least one metal compound to the at least one metal oxide.

Still other embodiments provide a sensor or a component thereof comprising at least one metal oxide, wherein the at least one metal oxide has been made by a process comprising:
 applying at least one metal compound to a substrate, and
 converting at least some of the at least one metal compound to the at least one metal oxide.

Additional embodiments provide a method for detecting at least one analyte, comprising providing at least one sensor for the at least one analyte, wherein the at least one sensor comprises at least one metal oxide made by a process comprising:
applying at least one metal compound to a substrate, and converting at least some of the at least one metal compound to the at least one metal oxide; and
passing at least one ion through the at least one metal oxide to detect the at least one analyte.

These and other embodiments are described in greater detail in the detailed description which follows.

DETAILED DESCRIPTION

Figure 1:
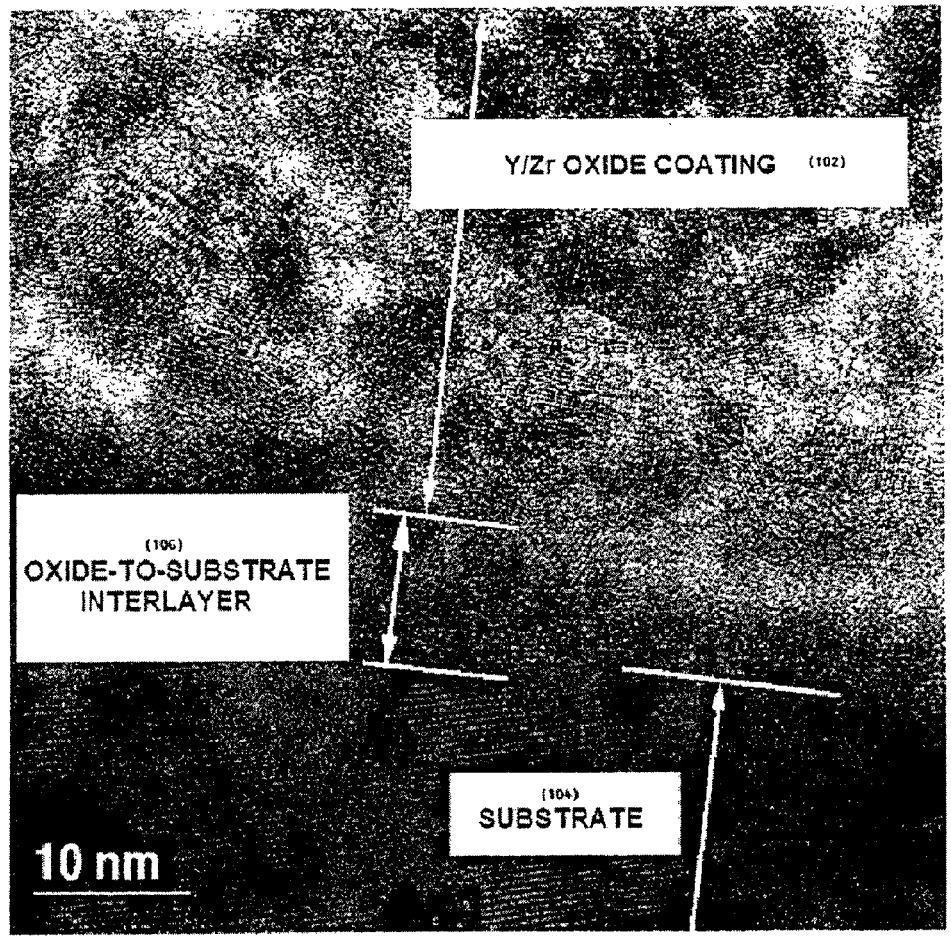
FIG. 1 is a micrograph at approximately 2 million× magnification that illustrates a thin film of yttria-stabilized zirconia ("YSZ": a material that can be used to produce ceramic electrolytes in solid oxide cells) with an interlayer (106) between the pure YSZ thin film (102) and the pure stainless steel (grade 304) of the substrate (104). The mixed YSZ-oxide & substrate interlayer (106) appears between the lower steel substrate layer (104) and the upper YSZ-oxide layer (102). As used herein, "interlayer" and "transition layer" are used interchangeably.

The present invention provides solid oxide cells and methods of making and using the same.

In some embodiments, solid oxide cells of the present invention demonstrate lower operating temperatures. Lowering the operating temperature of solid oxide cells enables the cells to be constructed from less expensive materials thereby rendering their production more cost friendly. In addition to cost savings, solid oxide cells having lower operating temperature can find application in a wider variety of fields. Furthermore, lower operating temperatures reduce stress on the individual components of the cell thereby reducing the onset of degradation pathways (such as cracking or delamination) that result from variances in coefficients of thermal expansion among dissimilar types of materials that comprise the component layers—or that result from excessive grain growth arising from exposure to high process ("sintering") or operating temperatures.

Furthermore, it would be desirable to lower the operating temperature of a solid oxide cell so that metals (instead of ceramics) can be used for electrode substrate construction. Metals generally have a higher level of mechanical strength, so they can also have a higher porosity and yet maintain an adequate degree of structural strength that is needed for the solid oxide cell's integrity.

Current ceramic electrode materials allow for porosity levels in the range of 30% to 40%. When these porosity levels are exceeded, structural (i.e. mechanical) strength becomes too weak to support cell construction.

However, by using certain types of metals or metal carbides, the porosity of an electrode can be increased to a range of 40% to 80%. And yet, these porous metallic materials still retain sufficient mechanical strength to allow cell construction.

It would additionally be desirable to apply conformal nano-scale surface treatments or thin films onto these porous metallic materials. These conformal surface treatments reduce the pore-size to either micron- or submicron-sized dimensions. With the addition of these surface treatments, the active surface area of an electrode component can increase the efficiency of the thus-treated electrode by as much as an order of magnitude.

This is particularly true if the surface treatments or thin films also exhibit a surface catalytic effect in addition to the efficiency improvements of modified surface area noted above. The catalytic effect of the surface treatments or thin films, in some embodiments, can be adjusted to enhance operating efficiency of the solid oxide cell and, thus, to lower operating temperature. In other embodiments, solid oxide cells of the present invention demonstrate greater tolerance for high operating temperatures. That greater tolerance enables such cells to be constructed from less expensive materials, and may increase service lifetime. The increased tolerance for high operating temperatures stems from the greater matching of coefficients of thermal expansion available to at least some embodiments of the present invention.

In still other embodiments, solid oxide cells exhibit increased operational efficiency due to decreased electrolyte thicknesses. Thinner electrolytes allow for lower energy losses due to ion diffusion through the electrolyte. Some embodiments of the present invention include a solid oxide electrolyte having a thickness of 100-1000 times thinner than ceramic electrolytes made according to conventional methods.

I. Solid Oxide Cells Useful as Fuel Cells

In one embodiment, the present invention provides a solid oxide fuel cell comprising an air electrode, a fuel electrode, an electrolyte interposed between the air electrode and the fuel electrode, and at least one electrode-electrolyte transition layer. In some embodiments of the present invention, an electrode-electrolyte transition layer is interposed between an electrode and the electrolyte. An electrode-electrolyte transition layer, in some embodiments, is interposed between the air electrode and the electrolyte. In other embodiments, an electrode-electrolyte transition layer is interposed between the fuel electrode and the electrolyte. In a further embodiment, a solid oxide fuel cell comprises a first electrode-electrolyte transition layer interposed between the air electrode and the electrolyte and a second electrode-electrolyte transition layer interposed between the fuel electrode and the electrolyte.

Turning now to components that can be included in solid oxide fuel cells, solid oxide fuel cells of the present invention comprise an air electrode. The air electrode of a solid oxide fuel cell operates as a cathode to reduce oxygen molecules thereby producing oxygen anions for subsequent transport through the electrolyte. In some embodiments, an air electrode comprises p-type semiconducting oxides such as lanthanum manganite ($LaMnO_3$). Lanthanum manganite can be doped with rare earth elements, such as strontium, cerium, and/or praseodymium to enhance conductivity. In one embodiment, an air electrode comprises $La_{1-x}Sr_xMnO_3$ [lanthanum strontium doped manganite (LSM)]. In another embodiment, an air electrode comprises lanthanum strontium ferrite or lanthanum strontium cobaltite or a combination thereof.

Air electrodes, according to some embodiments of the present invention, are porous. In one embodiment, an air electrode has a porosity ranging from about 5% to about 30%. In another embodiment, an air electrode has a porosity ranging from about 10% to about 25% or from about 15% to about 20%. In a further embodiment, an air electrode has a porosity greater than about 30%. An air electrode, in some embodiments, has a porosity ranging from about 30% to about 60% or from about 40% to about 80%. In one embodiment, an air electrode has a porosity greater than about 80%.

A lower operating temperature allows non-ceramic materials such as metals and metal carbides to be used. Since these materials generally possess higher levels of mechanical or structural strength at the lower operating temperatures, they can have higher levels of porosity than either ceramics (such as the LSM that can be used for cathodes) or cermets (such as mixtures of nickel and zirconia that can be used for anodes).

Metallic materials also tend to be easier to fabricate; and, they do not require high process (or 'sintering') temperatures. Such high process temperatures can result in detrimental micro-structural grain growth, which can occur both in previously processed ceramic and in the metallic components of the fuel cell.

Additionally, films for surface modification of air electrodes can have any desired thickness. In one embodiment, a thin film applied to an air electrode has a thickness ranging from about 10 nm to about 1 micron. In another embodiment, an air-electrode-film has a thickness ranging from about 10 nm to about 50 nm, from about 50 nm to about 750 µm, from about 50 nm to about 500 nm, from about 500 nm to about 500 µm, from about 1 µm to about 350 µm, or from about 10 µm to about 200 µm. In a further embodiment, an air electrode has a thickness ranging from about 50 µm to about 100 µm.

These thin films are used in some embodiments to modify the surface of porous air electrodes (cathodes) that, themselves, can be composed of porous metals or metal carbides. By using a non-ceramic porous material (such as a metal or metal carbide) as the body (or substrate) onto which a thin film is applied, many of the adverse structural and processing conditions of ceramic materials (such as high sintering temperatures) can be avoided. In addition, the operating efficiency of a solid oxide fuel cell comprised of these metallic and metallic carbide materials can also be significantly enhanced.

In addition to an air electrode, a solid oxide fuel cell comprises a fuel electrode. A fuel electrode, in some embodiments, comprises one or more metal oxides combined with one or a plurality of catalytic materials. Catalytic materials, as provided herein, comprise transition metals including, but not limited to, platinum, palladium, rhodium, nickel, cerium, gold, silver, zinc, lead, ruthenium, rhenium, or mixtures thereof. In one embodiment, a fuel electrode comprises zirconia ($ZrO_2$) combined with Ni. Yttria-stabilized zirconia (YSZ), $Zr_{(1-x)}Y_xO_{[2-(x/2)]}$, for example, can be combined with Ni to produce a Ni-YSZ fuel electrode. Catalytic materials, in some embodiments, are incorporated into metal oxide compositions of fuel electrodes in an amount ranging from about 0.5 to about 10 weight percent. In other embodiments, catalytic materials are incorporated into metal oxide compositions of fuel electrodes in an amount less than about 5 weight percent, less than about 0.5 weight percent, or greater than about 10 weight percent.

Fuel electrodes, according to some embodiments of the present invention, are porous. In one embodiment, a fuel electrode has a porosity ranging from about 5% to about 40%. In another embodiment, a fuel electrode has a porosity ranging from about 10% to about 30% or from about 15% to about 25%. In a further embodiment, a fuel electrode has a porosity greater than about 40%. A fuel electrode, in some embodiments, has a porosity ranging from about 40% to about 80%. In still other embodiments, a fuel electrode has a porosity greater than about 80%.

Additionally, the films used to treat the surface of fuel electrodes (or anodes) can have any desired thickness. In one embodiment a fuel electrode film has a thickness ranging from about 10 nm to about 1 micron. In another embodiment, the thickness of the film applied to the surfaces of a fuel electrode has a thickness ranging from about 50 nm to about 2 microns; or, from about 500 nm to about 1.5 microns; or, from about 750 nm to about 1 micron.

An electrolyte for solid oxide cells, for example interposed between the fuel electrode and the air electrode in some embodiments, comprises one or a plurality of layers of one or more metal oxides. In some embodiments, metal oxides suitable for electrolyte layers comprise zirconium oxides combined with various transition and/or rare earth metals, including, but not limited to, scandium, yttrium, erbium, ytterbium, europium, gadolinium, or dysprosium, or combinations thereof. In one embodiment, a metal oxide suitable for one or more layers of an electrolyte comprises zirconium oxide ($ZrO_2$) or yttria-stabilized zirconia (YSZ) $Zr_{(1-x)}Y_xO_{[2-(x/2)]}$, $x=0.08-0.11$. In another embodiment, a suitable electrolyte metal oxide comprises scandia-stabilized zirconia (SSZ) $Zr_{(1-x)}Sc_xO_{[2-(x/2)]}$, $x=0.09-0.11$. Additional suitable electrolyte zirconium compounds comprise zirconium silicate ($ZrSiO_4$), $Zr_{0.85}Ca_{0.15}O_{1.85}$ or $3ZrO_2 2CeO_2+10\% CaO$.

In another embodiment, metal oxides of an electrolyte comprise cerium oxides of the general formula $Ce_{(1-x)}M_xO_{(2-\delta)}$. In some embodiments M is samarium or gadolinium to produce $CeO_2-Sm_2O_3$ or $CeO_2-Gd_2O_3$.

Additional metal oxides suitable for electrolyte layers of solid oxide cells of the present invention comprise perovskite structured metal oxides. In some embodiments, perovskite structured metal oxides comprise lanthanum gallates ($LaGaO_3$). Lanthanum gallates, in some embodiments, are doped with alkaline earth metals or transition metals, or combinations thereof. In another embodiment, a perovskite structure metal oxide comprises lanthanum strontium gallium magnesium oxide (LSGM) $La_{(1-x)}Sr_xGa_{(1-y)}Mg_yO_{(3-\delta)}$, $x=0.10-0.20$, $y=0.15-0.20$.

In a further embodiment, metal oxides suitable for electrolyte layers comprise brownmillerites, such as barium indiate ($Ba_2In_2O_6$), non-cubic oxides such as lanthanum silicate, neodymium silicate, or bismuth based oxide, or combinations thereof.

Layers of an electrolyte, in some embodiments, are constructed independently and without reference to one another. As a result, a plurality of electrolyte layers can display the same compositional construction or different compositional constructions. Thus, for example, a compositional gradient can be introduced into an electrolyte in the following manner. An electrode material is chosen, such as, for example, LSM. An electrolyte material is also chosen, such as, for example, YSZ. To make the YSZ electrolyte, as will be further explained below, metal compounds containing yttrium and zirconium and possibly others will be applied to the surface of the electrode and converted into the corresponding metal oxides. This application and conversion can be repeated to form more than one layer of electrolyte on the electrode. Accordingly, metal compounds corresponding to the material of the electrode can be included in the applying step forming the first layers of the electrolyte. In this example, lanthanum compounds, strontium compounds, manganese compounds, and combinations thereof can be applied to the electrode surface along with the yttrium compounds and zirconium compounds, to impart a concentration of species corresponding to the electrode material in the electrolyte. As subsequent layers of electrolyte are formed, the concentration or amount of lanthanum compounds, strontium compounds, manganese compounds, and combinations thereof applied to the electrode (more accurately, to the previously-formed layer(s) of electrolyte) are decreased. If desired, the concentration of species corresponding to the electrode material in the electrolyte can be decreased to zero in subsequent layers of electrolyte, or the compositional gradient can assume any desired profile across the electrolyte. The species corresponding to the electrode material in the electrolyte can be any suitable species in any suitable dispersion, such as, for example, metal oxides, ionic impurities, solid solutions, distinct domains, and the like.

Electrolyte layers of solid oxide cells, according to some embodiments of the present invention, comprise a plurality of nanocrystalline grains, the nanocrystalline grains comprising one or more of the metal oxides that are suitable for use as an electrolyte in a solid oxide cell. In some embodiments, the nanocrystalline grains have an average size of less than about 50 nm. In other embodiments, nanocrystalline grains of electrolyte layers have an average size ranging from about 2 nm to about 40 nm or from about 3 nm to about 30 nm. In another embodiment, nanocrystalline grains have an average size ranging from about 10 nm to about 25 nm. In a further embodiment, nanocrystalline grains have an average size less than about 10 nm or less than about 5 nm.

Electrolytes of solid oxide cells are substantially non porous, in some embodiments. In one embodiment, an electrolyte has a porosity less than about 20%. In another embodiment, an electrolyte has a porosity less than about 15% or less than about 10%. In a further embodiment, an electrolyte has a porosity less than about 5% or less than about 1%. In one embodiment, an electrolyte is fully dense meaning that the electrolyte has no porosity.

In some embodiments, an electrolyte has a thickness ranging from about 1 nm to about 1 mm or from about 10 nm to about 500 μm. In other embodiments, an electrolyte has a thickness ranging from about 50 nm to about 250 μm, from about 100 nm to about 100 μm, or from about 500 nm to about 50 μm. In another embodiment, an electrolyte has a thickness ranging from about 750 nm to about 10 μm, or from about 1 μm to about 5 μm, or from about 1.2 μm to about 4 μm, or from about 1.5 μm to about 2 μm. In a further embodiment, an electrolyte has a thickness less than about 10 μm or less than about 1 μm. In one embodiment, an electrolyte has a thickness ranging from about 1 nm to about 100 nm or from about 50 nm to about 100 nm. In still other embodiments, an electrolyte has a thickness greater than about 500 μm.

In some embodiments wherein an electrolyte comprises a plurality of layers, each layer has a thickness ranging from about 3 nm to about 15 nm, wherein the total thickness of the electrolyte is the summation of the thicknesses of the individual layers. In other embodiments, a layer of electrolyte can have a thickness less than about 3 nm or greater than about 15 nm.

Materials suitable for use in air electrodes, fuel electrodes, electrolyzer electrodes, sensors, and/or electrolytes, in addition to the materials recited hereinabove, can be chosen from $CeO_2$—$ZrO_2$ wherein $CeO_2$ is about 10-90 weight percent; yttria-stabilized zirconia (YSZ) wherein yttria is present in an amount of about 1-50 mol percent; $CeO_2$—$PrO_2$ wherein $PrO_2$ is up to about 50 weight percent; $PrO_2$—$CeO_2$—$ZrO_2$ wherein $PrO_2$—$CeO_2$ is up to about 90 weight percent; $PrO_2$—$ZrO_2$ wherein $PrO_2$ is 10 to 90 weight percent; scandia-doped zirconia (SSZ) doped with one or more of $Co_3O_4$, $Bi_2O_3$, $SiO_2$, $TiO_2$, $Fe_2O_3$, $NiO$, $MnO_2$, $CeO_2$, and $Al_2O_3$; YSZ doped with one or more of $Co_3O_4$, $Bi_2O_3$, $SiO_2$, $TiO_2$, $Fe_2O_3$, $NiO$, $MnO_2$, $CeO_2$, and $Al_2O_3$; CaO stabilized zirconia doped with one or more of $Co_3O_4$, $Bi_2O_3$, $SiO_2$, $TiO_2$, $Fe_2O_3$, $NiO$, $MnO_2$, $CeO_2$, and $Al_2O_3$; mixed LSM and YSZ; and combinations thereof.

Oxides of the following elements can be used in embodiments of air electrodes, fuel electrodes, electrolyzer electrodes, sensors, and/or electrolytes in some embodiments of the present invention: lithium, beryllium, sodium, magnesium, aluminum, silicon, potassium, calcium, scandium, titanium, vanadium, chromium, manganese, iron, cobalt, nickel, copper, zinc, gallium, germanium, arsenic, bromine, rubidium, strontium, yttrium, zirconium, niobium, molybdenum, technetium, ruthenium, rhodium, palladium, antimony, tellurium, silver, cadmium, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, irridium, gold, mercury, thallium, lead, bismuth, radium, actinium, platinum, thorium, protactinium, uranium, neptunium, plutonium, americium, berkelium, californium, einsteinium, fermium, mendelevium, nobelium, lawrencium, or curium. Oxides containing more than one of the foregoing elements, and oxides containing elements in addition to the foregoing elements, also can be used in embodiments of the present invention.

Moreover, in some embodiments, catalytic metals can be incorporated into each of the foregoing metal oxide materials in an amount ranging from about 0.5 to about 10 weight percent. In other embodiments, catalytic metals can be incorporated in an amount less than about 5 weight percent.

In some embodiments of solid oxide cells of the present invention, an electrode-electrolyte transition layer is interposed between the electrolyte and the electrode. An electrode-electrolyte transition layer comprises both electrode and electrolyte materials. By comprising both electrode and electrolyte materials, the electrode-electrolyte transition layer, in some embodiments, is operable to reduce disparities in coefficients of thermal expansion between the electrode and electrolyte. Reducing such disparities can have an inhibitory effect on degradative pathways such as cracking or delamination between the electrode and electrolyte. Moreover, an electrode-electrolyte transition layer provides increased stability by anchoring the electrolyte to the electrode. The electrode-electrolyte transition layer, in some embodiments, additionally provides a robust base on which to further build an electrolyte, the electrolyte having thickness less than about 10 μm or less than about 1 μm.

In some embodiments, an electrode-electrolyte transition layer has a thickness ranging from about 50 nm to about 100 nm or from about 20 nm to about 80 nm. In another embodiment, an electrode-electrolyte transition layer has a thickness ranging from about 30 nm to about 60 nm or from about 40 nm to about 50 nm. In a further embodiment, an electrode-electrolyte transition layer has a thickness less than about 10 nm or greater than about 100 nm.

FIG. 1 is a micrograph at approximately 2 million× magnification illustrating an electrode-electrolyte transition layer according to one embodiment of the present invention. In the micrograph, a YSZ electrolyte (102) is disposed on an electrode substrate (104) made of stainless steel 304. An electrode-electrolyte interlayer (106) is interposed between the YSZ electrolyte (102) and the electrode substrate (104).

In some embodiments, a solid oxide fuel cell comprising an air electrode, a fuel electrode, an electrolyte interposed between the air electrode and the fuel electrode, and optionally at least one electrode-electrolyte transition layer has an operating temperature less than about 1000° C. or less than about 900° C. In another embodiment, a solid oxide fuel cell of the present invention has an operating temperature of less than about 800° C., less than about 700° C., less than about 600° C., or less than about 500° C. In a further embodiment, a solid oxide fuel cell of the present invention has an operating temperature of less than about 300° C.

II. Solid Oxide Cells Useful as Electrolyzers

Some embodiments of the present invention provide solid oxide electrolyzer cells or a component thereof comprising at least one metal oxide. In certain embodiments, the at least one electrolyzer cell or a component thereof is substantially identical in manufacture and composition as the fuel cells and components described above.

In some of those embodiments of the present invention where the same cell can function as an electrolyzer cell and alternately as a fuel cell simply by reversing the flow of electrons, the cathode of the electrolyzer corresponds to the fuel electrode of the fuel cell; and the anode of the electrolyzer corresponds to the air electrode of the fuel cell. Those of ordinary skill in the art recognize that oxidation occurs at the anode, and reduction occurs at the cathode, so the name of a given electrode may differ depending on whether the cell is operating as an electrolyzer or as a fuel cell.

In other embodiments, electrons flow in the same direction, regardless of whether the cell is electrolyzing or producing electricity. This can be accomplished, for example, by supplying oxygen anions to a given electrode in electrolysis mode, and alternately supplying hydrogen to the same electrode in fuel cell mode. Such an electrode will function as the oxidizing anode in either mode.

Accordingly, some embodiments of the present invention provide a solid oxide electrolyzer cell, comprising at least one first electrode, at least one second electrode, and at least one electrolyte interposed between the first electrode and the second electrode. The cell optionally contains at least one electrode-electrolyte transition layer, at least one composition gradient, at least one porosity gradient, or a combination thereof. In some embodiments, the at least one electrolyte is made by applying a metal compound composition to a substrate, and converting at least some of the metal compound composition to at least one metal oxide.

The present invention also provides, in some embodiments, a method for making at least one product, comprising: providing at least one solid oxide cell comprising at least one first electrode, at least one second electrode, and at least one metal oxide interposed between the at least one first electrode and at least one second electrode;
contacting the at least one first electrode with at least one reactant; and
supplying electrical energy to the at least one first electrode and the at least one second electrode thereby causing the at least one reactant to undergo electrochemical reaction to yield the at least one product.

The skilled electrochemist will appreciate that a complete circuit is necessary for electrical energy to cause electrochemical reaction. For example, at least one ion may traverse the metal oxide electrolyte to complete the electrical circuit at the second electrode. Moreover, at least one second product may be formed at the second electrode due to electrochemical reaction. Therefore, some embodiments further provide for contacting the at least one second electrode with at least one second reactant, thereby causing the at least one second reactant to undergo electrochemical reaction to yield at least one second product. Contacting an electrode and supplying electrical energy can occur in any suitable order. In a continuous process, electrical energy supply is maintained while additional reactant(s) enter the cell and product(s) are removed.

Any suitable reactant can be supplied to an electrode for electrochemical reaction. Suitable reactants include, but are not limited to, water such as, for example, pure water, fresh water, rain water, ground water, salt water, purified water, deionized water, water containing at least one ionic substance, brine, acidified water, basified water, hot water, superheated water, steam, carbon dioxide, carbon monoxide, hydrogen, nitrous oxides, sulfur oxides, ammonia, metal salts, molten metal salts, and combinations thereof. Ionic substances include those substances that release at least one ion when placed in contact with water, and include, but are not limited to, salts, acids, bases, and buffers. Reactants, and for that matter, products, can be in any suitable form, including solid, liquid, gas, and combinations thereof. Solid reactants and/or solid products lend themselves to batch processes, although suitable methods for removing a solid product from a cell can be employed. Fluid reactants and products can appear in either batch or continuous processes. Optionally, heat energy is applied to the reactant, the product, at least one electrode, the at least one metal oxide, the cell, or a combination thereof.

Some embodiments provide at least one sacrificial electrode. A sacrificial electrode itself reacts in the electrolysis process, and is thereby consumed or rendered unreactive as the reaction proceeds. For example, a zinc electrode can be consumed in a suitable solid oxide cell reaction, yielding $Zn^{2+}$ and two electrons per mole of zinc consumed. In another example, an electrode can become coated and thereby rendered unreactive by solid product forming on its surface. The unreactive electrode can be removed from the cell, and the product extracted from the electrode, or the product can be used on the electrode in another process. The electrode then can be regenerated, recycled, or discarded. Alternatively, a sacrificial electrode can be made to gradually insert into a cell at a rate consistent with the rate at which the electrode is consumed.

A reactant undergoing electrochemical reaction can be oxidized and/or reduced, and chemical bonds may form and/or break. For example, when water undergoes electrolysis, hydrogen-oxygen bonds break, $H^+$ is reduced to $H^0$, $O^{2-}$ is oxidized to $O^0$, and $H_2$ and $O_2$ form, in some circumstances. Hydrogen peroxide and other species may form in other circumstances. The skilled artisan will appreciate that many electrode half reactions can be substituted so that any variety of anions, cations, and other species may result from electrochemical reaction.

In one embodiment, water containing NaCl can be electrolyzed to form hydrogen gas and NaOH at the cathode, and chlorine gas at the anode, in the so-called chlor-alkali process:

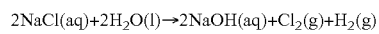
$$2NaCl(aq) + 2H_2O(l) \rightarrow 2NaOH(aq) + Cl_2(g) + H_2(g)$$

A solid oxide cell arranged to carry out that reaction, in some embodiments, provides water containing a high concentration of NaCl (for example, saturated) to a first electrode that will act as an anode, and provides water to a second electrode that will act as a cathode. The cell also provides liquid effluent collection to remove the depleted NaCl solution from the anode, and NaOH-containing water from the cathode. The cell further provides gas effluent collection to remove chlorine gas from the anode and hydrogen gas from the cathode. Optionally, the hydrogen and chlorine can be subject to electrochemical reaction to release the electrochemical energy stored by the foregoing electrolysis, or they can be used for other industrial processes, such as the synthesis of sodium hypochlorite.

The present invention also provides methods for storing electrochemical energy. In some embodiments, at least one reactant is supplied to at least one electrode of a solid oxide cell, the at least one reactant undergoes one or more electrochemical reactions and yields at least one fuel, thereby storing electrochemical energy. The electrochemical reaction may also yield other products, such as cations, anions, and other species, some of which may form at a second electrode of the solid oxide cell that completes an external circuit. At least one first electrode and at least one second electrode are separated by at least one metal oxide electrolyte in the solid oxide cell. The fuel can be subjected to energy conversion processes such as reverse electrochemical reaction in a fuel cell or battery, combustion, and the like to release the stored electrochemical energy.

In one embodiment, electrochemical energy is stored by providing a reactant to at least one cathode; reducing the reactant at the at least one cathode to release at least one anion and at least one fuel; storing the at least one fuel; transporting the at least one anion through at least one metal oxide electrolyte to at least one anode; and oxidizing the at least one anion. Optionally, the oxidized anion is stored as well, separately from the stored fuel. Thus, in one embodiment, water in a suitable form is supplied to a cathode, at which it is reduced to hydrogen ($H_2$) and oxygen anion ($O^{2-}$); the hydrogen is collected and stored, while the oxygen anion diffuses through a solid metal oxide electrolyte to an anode where the oxygen anion is oxidized to oxygen ($O_2$). Optionally, in the foregoing non-limiting example, the oxygen is collected and stored as well.

When desired, the stored hydrogen can be fed to any suitable fuel cell, including but not limited to the cell that produced the hydrogen, and the hydrogen can be oxidized to release the stored electrochemical energy. Any suitable gas can be fed to the air electrode of the fuel cell, such as, for example, the optionally-stored oxygen, other oxygen, other oxygen-containing gas such as air, and combinations thereof. Alternatively, the stored hydrogen can be combusted with oxygen to propel a rocket, drive a piston, rotate a turbine, and the like. In other embodiments, the stored hydrogen can be used in other industrial processes, such as petroleum cracking.

Some embodiments involve those reactants that yield the high energy materials commonly found in primary (nonrechargeable) and secondary (rechargeable) batteries. For secondary battery materials, the low-energy (discharge) state materials may be produced, since secondary batteries can be charged before first use. Such materials include, but are not limited to, $MnO_2$, $Mn_2O_3$, $NH_4Cl$, $HNO_3$, $LiCl$, $Li$, $Zn$, $ZnO$, $ZnCl_2$, $ZnSO_4$, $HgO$, $Hg$, $NiOOH$, $Ni(OH)_2$, $Cd$, $Cd(OH)_2$, $Cu$, $CuSO_4$, $Pb$, $PbO_2$, $H_2SO_4$, and $PbSO_4$.

At least some embodiments of fuel cells described above can be used to provide electrolyzer cell embodiments of the present invention. While fuel cell embodiments optionally employ one or more of fuel supply, air or oxidizer supply, interconnects, and electrical energy harvesting means (e.g., wires forming a circuit between the fuel and air electrodes' interconnects), electrolyzer cell embodiments optionally employ one or more of reactant supply, fuel collection, interconnects, and electrical energy supply. Optionally, electrolyzer cell embodiments also provide collection means for other products in addition to fuel. The reactant supply provides any suitable reactant for electrolysis. Fuel collection, in some embodiments, involves collecting hydrogen for storage and later use. Storage vessels, metal hydride technology, and other means for storing hydrogen are known in the art. Fuel collection, in other embodiments, involves collection of, for example, carbon-coated electrodes for later oxidation. Alternatively, carbon can be formed into fluid hydrocarbon for easy storage and later combustion or reformation. Hydrocarbon formation requires a supply of hydrogen molecules, atoms, or ions in a suitable form to combine with carbon at the cathode, in some embodiments. Other product collection involves, in some embodiments, the collection of oxygen for storage and later use. In still other embodiments, an electrolyzer cell is capable of performing other electrolysis tasks, such as electroplating. In such embodiments, at least one metal oxide functions as a solid electrolyte shuttling at least one ion to complete an electrical circuit.

In some embodiments, the electrodes of the electrolyzer cell are adapted for the particular electrochemistry expected to occur at the given electrode. For example, the electrode can comprise one or more catalytic materials to facilitate the electrochemical reaction. Catalytic materials can comprise transition metals including, but not limited to, platinum, palladium, rhodium, nickel, cerium, gold, silver, zinc, lead, ruthenium, rhenium, or mixtures thereof. Catalytic materials, in some embodiments, are disposed in one or a plurality of metal oxide layers coating the electrode. In another example, the electrode can exhibit increased surface area, for example, with porosity, electrode geometry, or a combination thereof. Electrodes comprising catalytic materials can optionally demonstrate compositional gradients based on the distribution of the catalytic materials in a plurality of metal compound layers proximal to the electrodes. In one embodiment, an electrode comprises a substrate and a plurality of metal oxide layers disposed on the substrate, wherein metal oxide layers proximal to the substrate comprise greater amounts of catalytic material than metal oxide layers distal to the substrate. Moreover, in another embodiment, metal oxide layers distal to the substrate comprise greater amounts of catalytic material than metal oxide layers proximal to the substrate.

Solid oxide cells acting as electrolyzers operate at any suitable temperature. In some embodiments, a solid oxide cell comprising a first electrode, a second electrode, an electrolyte interposed between the first electrode and the second electrode, and optionally at least one electrode-electrolyte transition layer has an operating temperature less than about 1000° C. or less than about 900° C. In another embodiment, a solid oxide cell of the present invention has an operating temperature of less than about 800° C., less than about 700° C., less than about 600° C., or less than about 500° C. In a further embodiment, a solid oxide cell of the present invention has an operating temperature of less than about 300° C., less than about 200° C., less than about 100° C., less than about 50° C., or less than about 25° C.

III. Solid Oxide Cells Useful as Sensors

Some embodiments of the present invention provide solid oxide sensors or components thereof. Like the fuel cells and electrolyzer cells described above, sensors of the present invention comprise at least one metal oxide. In some embodiments, at least one ion passes through that metal oxide during cell operation. In other embodiments, the solid oxide cells useful as sensors or components thereof are substantially identical to the solid oxide cells and components described above. The metal oxide of sensors in certain embodiments has been made according to a process comprising:

applying at least one metal compound to a substrate, and
converting at least some of the at least one metal compound to the at least one metal oxide.

Sensors according to various embodiments of the present invention can be used to detect any suitable analyte or analytes. Oxygen sensors, useful as lambda sensors in automotive exhaust systems, or as oxygen partial pressure detectors in rebreather systems, represent some applications for embodiments. Other sensors, such as gas sensors including but not limited to $CO$, $CO_2$, $H_2$, $NO_x$, and $SO_x$; ion sensors including but not limited to pH meters, $K^+$, and $Na^+$; biosensors including but not limited to glucose sensors and other enzyme electrodes; electrochemical breathalyzers; and electronic noses; represent other applications for embodiments of the present invention. Many such sensors function at least in part due to the diffusion of an ion through an electrolyte, which electrolyte comprises at least one metal oxide. Accordingly, additional embodiments provide a method for detecting at least one analyte, comprising:

providing at least one sensor for the at least one analyte, wherein the at least one sensor comprises at least one metal oxide made by a process comprising:
  applying at least one metal oxide to a substrate, and
  converting at least some of the at least one metal compound to the at least one metal oxide; and
passing at least one ion through the at least one metal oxide to detect the at least one analyte. Passing an ion through a metal oxide can include any suitable transport mechanism, such as, for example, diffusion. In addition, movement along metal oxide crystal grain boundaries represents another transport mechanism, in some embodiments. Detecting an analyte can indicate obtaining any useful information about the analyte, such as, for example, determining its mere presence, concentration, partial pressure, oxidation state, or combinations thereof. And, sensors of the present invention can be designed for any suitable environment, such as solid, semisolid (e.g., soil), liquid, gas, plasma, and combinations thereof. Also, such sensors can be designed for any suitable operating temperature, ranging from the very cold to the very hot. Some solid oxide cells useful as sensors according to the present invention have an operating temperature of below about $-195°$ C., below about $-182°$ C., below about $-77°$ C., from about $-78°$ C. to about $0°$ C., from about $0°$ C. to about $100°$ C., from about $100°$ C. to about $400°$ C., from about $400°$ C. to about $600°$ C., from about $600°$ C. to about $900°$ C., from about $900°$ C. to about $1200°$ C., or above about $1200°$ C. Other embodiments useful as sensors have operating temperatures below about $0°$ C., above about $0°$ C., above about $100°$ C., or above about $500°$ C.

A few embodiments of the present invention provide solid oxide cells, useful as sensors, that enjoy one or more advantages over conventional sensors. In some embodiments, the at least one metal oxide has a certain thickness, thinner than conventional sensors. In other embodiments, the solid oxide cell operates at a lower temperature, compared to conventional sensors. Still other embodiments provide smaller sensors. Even other embodiments provide sensors made from less-expensive materials. Additional embodiments have better-matched coefficients of thermal expansion between two or more materials in the cell. Still other embodiments provide one or more concentration gradients, one or more porosity gradients, or combinations thereof.

Further embodiments of the present invention provide a sensor comprising at least two electrodes separated by at least one metal oxide that functions as a solid electrolyte. In some of those embodiments, the voltage difference between the at least two electrodes corresponds to the concentration of the analyte being detected at one of the electrodes. A first electrode functions as a reference electrode, and is exposed to a reference environment. Suitable reference environments include, but are not limited to, air, vacuum, standard solutions, and environments of known or controlled composition. In some embodiments, the reference environment is formed by arranging one or more materials that substantially isolate the reference electrode from the environment being measured. The second electrode is exposed to the environment being measured. Optionally, the second electrode comprises one or more catalytic materials. In some embodiments, at least one catalytic material is chosen from platinum, palladium, rhodium, nickel, cerium, gold, silver, zinc, lead, ruthenium, rhenium, and combinations thereof. In operation, the first and second electrodes are placed in electrical communication with one or more devices that can measure, for example, the voltage difference, the current, the resistance, or combinations thereof, between the two electrodes. Such devices are known in the art. Optionally, heat or cooling can be supplied to one or both electrodes, the electrolyte, or combinations thereof. Heat or cooling can come from any suitable source, such as, for example, one or more electrical resistance heaters, chemical reaction, thermal fluid in thermal communication with the sensor, the measured environment, and combinations thereof.

In some embodiments, a reference voltage is supplied to the electrodes, and the current needed to maintain the reference voltage corresponds to the concentration of the analyte being measured. For example, U.S. Pat. No. 7,235,171, describes two-electrode hydrogen sensors comprising barium-cerium oxide electrolyte. The '171 patent also indicates that various other metal oxides also function as electrolytes in hydrogen sensors, including selenium cerium oxides, selenium cerium yttrium oxides, and calcium zirconium oxides, which conduct protons, and oxygen anion conductors. The '171 patent is incorporated herein by reference.

In other embodiments, a gas permeable porous platinum measuring electrode is exposed to a measured environment that contains a partial pressure of oxygen. At least one metal oxide, such as, for example, yttria-stabilized zirconia, separates the measuring electrode from a gas permeable porous platinum reference electrode that is exposed to air. The voltage difference, current, or both between the electrodes can be measured and correlated to the difference of partial pressure of oxygen between the measured environment and air. In some embodiments, the measured environment is an exhaust stream from the combustion of hydrocarbons.

In still other embodiments, at least two pairs of electrodes appear, wherein at least one metal oxide separates the electrodes in each pair. One of the two pairs functions as a reference cell, while the other of the two pairs functions as a measuring cell, in some embodiments. Further embodiments provide, in a first pair of electrodes, a reference electrode exposed to a reference environment and a Nernst electrode exposed to the measured environment. At least one metal oxide that functions as a solid electrolyte is situated between the reference electrode and the Nernst electrode. In a second pair of electrodes, an inner pump electrode is separated from an outer pump electrode, with at least one metal oxide functioning as a solid electrolyte situated between the inner and outer pump electrodes. The inner pump electrode and the Nernst electrode are exposed to the environment to be measured optionally through a diffusion barrier. In operation, an external reference voltage is applied across the pump electrodes. The current needed to maintain the reference voltage across the pump electrodes provides a measure of the analyte concentration in the measured environment. For a conventional broadband lambda sensor containing such a pair of electrodes, see U.S. Pat. No. 7,083,710 B2, which is incorporated herein by reference in its entirety. Optionally, a sensor of the present invention is adapted to electrically communicate with control circuitry that smoothes operation of the sensor before the sensor has achieved standard operating conditions, such as temperature. See, for example, U.S. Pat. No. 7,177,099 B2, which is also incorporated herein by reference.

Thus, certain embodiments of the present invention provide so-called narrow band sensors such as lambda sensors that fluctuate between lean and rich indications. Other embodiments provide broadband sensors such as lambda sensors that indicate the partial pressure of oxygen, and thereby the degree of leanness or richness of an air-fuel mixture.

Some embodiments provide more than two electrodes. For example, a sensor according to the present invention may contain a plurality of measuring electrodes. For another example, a sensor may comprise a plurality of reference electrodes. In another example, a sensor may comprise, or be adapted to electrically communicate with, a standard electrode or other device providing information useful to the operation of the sensor.

In still other embodiments of the present invention, a sensor is made by applying at least one metal compound to a substrate, and converting at least some of the at least one metal compound to at least one metal oxide. Metal compounds include those described herein, such as, for example, metal carboxylates, metal alkoxides, and metal β-diketonates. Also, metal compounds containing at least one metal atom and combinations of two or more ligands can function as metal compounds.

In some embodiments, the at least one sensor or at least one component thereof can be made in any suitable manner. For example, the at least one metal oxide can be formed on any suitable substrate. Such substrates include, but are not limited to, one or more metals, plastics, ceramics, cermets, semiconductors, insulators, metal oxides, and combinations thereof. In some embodiments, the substrate is an electrode. At least one metal oxide is formed on the substrate by applying at least one metal compound to the substrate, and converting at least some of the at least one metal compound to at least one metal oxide. In some embodiments, the at least one metal compound is fully converted to at least one metal oxide. Certain embodiments provide porous substrates, while others provide non-porous substrates. Still other embodiments provide fluid-permeable substrates, while others provide substrates that are substantially impermeable to fluid.

In some embodiments, a plurality of metal oxide layers are formed on the substrate. In one embodiment, for example, a method of making a sensor or at least one component thereof comprises forming a plurality of metal oxide layers on the substrate, wherein each layer of metal oxide is formed on a preceding layer by applying a metal carboxylate composition to the preceding layer, the metal carboxylate composition comprising at least one metal salt of a carboxylic acid. The metal carboxylate composition is subsequently converted to at least one metal oxide, for example, by exposing the metal carboxylate composition to heat. In still other embodiments, the at least one metal compound comprises one or more of catalytic materials, nanoparticles, substrate materials, and the like. Yet other embodiments provide one or more concentration gradients, porosity gradients, transition layers, or combinations thereof.

Some embodiments of the present invention provide metal oxides that are permeable to ions such as $O^{2-}$ ions. Other embodiments provide metal oxides that may not necessarily be permeable to ions. Still other embodiments provide metal oxides that are permeable to ions, but such permeability is not required for the function of the metal oxide in the embodiment. For example, in certain embodiments, a metal oxide functions as a solid electrolyte in a gas sensor, allowing diffusion of ions during operation of the gas sensor. In other embodiments, a metal oxide functions as a structural element of the gas sensor. In still other embodiments, a metal oxide functions as both a solid electrolyte and a structural element of the gas sensor. In still other embodiments, one or more metal oxides are used alone or in combination, for one or more functions in a gas sensor.

IV. Solid Oxide Cells Comprising Compositional Gradients and Porosity Gradients

In order to reduce problems and disadvantages associated with variances in coefficients of thermal expansion between electrodes and electrolytes of solid oxide cells and to increase ionic conductivities, electrolytes of some embodiments of the present invention comprise compositional gradients. An electrolyte of a solid oxide cell, in one embodiment, comprises a region proximal to an electrode and a region distal to the electrode wherein the region proximal to the electrode comprises a greater amount of electrode material than the region distal to the electrode. An electrode, for example, comprises $La_{1-x}Sr_xMnO_3$ [lanthanum strontium doped manganite (LSM)]. The region of the electrolyte proximal to the electrode comprises greater amounts of LSM in comparison with the region of the electrolyte distal from the electrode.

In another embodiment, an electrolyte of a solid oxide cell comprises a plurality of metal oxide layers. Metal oxide layers of the electrolyte proximal to the electrode comprise greater amounts of electrode material than metal oxide layers of the electrolyte distal to the electrode. An electrode, for example, comprises a porous metal or metal carbide body (or substrate) onto which a thin film surface treatment has been applied and that consists of a material suitable for use as the air electrode (cathode) of a solid oxide fuel cell (such as LSM). Metal oxide layers of an electrolyte proximal to the electrode, in one embodiment, comprise greater amounts of LSM in comparison with metal oxide layers of the electrolyte distal from the electrode. Incorporating greater amounts of electrode material in electrolyte layers proximal or adjacent to the electrode in a solid oxide cell establishes a compositional gradient among the electrolyte layers. Such a compositional gradient can permit layers proximal to the electrode to demonstrate a coefficient of thermal expansion that better matches the coefficient of thermal expansion of the electrode. As a result, disparities in coefficients of thermal expansion between the electrode and the electrolyte can be reduced or eliminated leading to a more stable solid oxide cell. Reducing the variances in coefficients of thermal expansion between solid oxide cell component layers can reduce or inhibit degradative pathways such as electrode and/or electrolyte cracking as well as electrode/electrolyte delamination. Reduction or inhibition of these pathways results in a more stable and efficient cell.

In view of enhanced stabilities provided by a compositional gradient, in some embodiments, a solid oxide cell comprises a first electrode comprising a first material and an electrolyte comprising a first region proximal to the first electrode and a second region distal to the first electrode, wherein the first region of the electrolyte comprises a greater amount of the first material than the second region of the electrolyte.

In another embodiment, comprising a porous metal (or metal carbide) body (or substrate) onto which a thin film surface treatment has been applied and that comprises a first material, and an electrolyte comprising a plurality of layers of an electrolyte material, the layers of the electrolyte material proximal or adjacent to the first electrode further comprise a greater amount of the first material of the first electrode than layers of the electrolyte distal or spaced apart from the first electrode. The first material of the first electrode and the plurality of electrolyte layers, according to some embodiments of the present invention, can comprise any of the materials suitable for use as electrodes and/or electrolytes. Moreover, the first electrode and plurality of electrolyte layers can display any of the physical parameters, such as thickness, porosity, and average grain size, recited for electrodes and/or electrolytes hereinabove.

Additionally, in order to reduce problems and disadvantages associated with variances in coefficients of thermal expansion between electrode and electrolytes of solid oxide cells, electrodes, in some embodiments of the present invention comprise compositional gradients. An electrode, in one embodiment, comprises a region proximal to the electrolyte and a region distal to the electrolyte, wherein the region proximal to the electrolyte comprises a greater amount of electrolyte material than the region of the electrode distal to the electrolyte. In another embodiment, an electrode of a solid oxide cell comprises a plurality of layers. Layers of the electrode proximal to the electrolyte comprise a greater amount of electrolyte material than layers of the electrode distal to the electrolyte. A solid oxide cell, in some embodiments, comprises a first electrode comprising a plurality of layers of a first material and an electrolyte comprising an electrolyte material disposed on the first electrode, wherein layers of the first material proximal or adjacent to the electrolyte further comprise a greater amount of the electrolyte material than layers of the first material distal or spaced apart from the electrolyte.

The first material of the plurality of electrode layers and the electrolyte material, according to some embodiments of the present invention, can comprise any of the materials suitable for use as electrodes and/or electrolytes. Additionally, the electrolyte and plurality of electrode layers can display any of the physical parameters, such as thickness, porosity, and average grain size, recited for electrodes and/or electrolytes hereinabove.

In addition to variances in coefficients of thermal expansion, solid oxide fuel cells of some embodiments of the present invention also address fuel, air, reactant, and product delivery and removal mechanisms by providing electrodes comprising porosity gradients. Electrodes of solid oxide fuel cells are optionally porous in order to allow the ingress of air and fuel to the electrolyte and the egress of other gases produced or not consumed by the fuel cell. Similarly, electrodes of cells other than fuel cells may be porous, to allow for introduction of one or more reactants, and removal of one or more products, from the electrode. In one embodiment, a solid oxide cell comprises a solid electrolyte disposed on a first electrode, the first electrode comprising a first region proximal to the solid electrolyte and a second region distal to the electrolyte, wherein the first region has a porosity less than the second region. Alternatively, in another embodiment, the first region of the electrode has a porosity that is greater than the second region of the electrode.

Moreover, in another embodiment, a solid oxide cell comprises a first electrode comprising a plurality of layers of a first material and an electrolyte disposed on the first electrode, wherein layers of the first material proximal to the electrolyte have porosities less than layers of the first material distal to the electrolyte. In one embodiment, for example, layers of the first material proximal to the electrolyte have a porosity ranging from about 5 percent to about 10 percent while layers of the first material distal to the electrolyte have a porosity ranging from about 40 to about 70 percent. Alternatively, in another embodiment, layers of the first material proximal to the solid electrolyte have porosities greater than layers of the first material distal to the solid electrolyte.

Establishing a porosity gradient among a plurality of layers of an electrode permits the electrode to better match the porosity of the electrolyte without producing a pore structure within the electrode that is unduly restrictive to air, fuel, reactant, or product flow. Porosity can be controlled by any suitable method, such as, for example, by including particles such as nanoparticles in the compositions used to manufacture an electrode or electrolyte, pore-forming agents that release gas during manufacture, substances that can be dissolved, melted, or sublimed and thereby removed after a given layer has been manufactured, and combinations thereof. In some embodiments, one or more organic compounds such as corn starch can be included in the composition, which organic compounds are burned away upon sintering in the presence of oxygen to leave a porous structure upon cooling. A porosity gradient is established by including an increasing or decreasing amount of pore-forming agent in the compositions used to form subsequent layers of electrode or electrolyte, for example.

V. Electrodes of Solid Oxide Cells

In another aspect, the present invention provides electrodes operable to be used in solid oxide cells as well as other applications. Electrodes of the present invention, in some embodiments, are resistant to harsh environments and various chemical species which can foul the electrodes, such as sulfur and carbon. In one embodiment, the present invention provides an electrode comprising a substrate comprising a first material, a coating comprising at least one layer of at least one metal oxide disposed on the substrate, and a substrate-coating transition layer interposed between the substrate and the coating. In some embodiments, a coating comprises a plurality of layers of at least one metal oxide disposed on the substrate. An electrode, in one embodiment, is an anode. An electrode in another embodiment is a cathode. In some embodiments, the metal oxide coating of an electrode can protect the electrode substrate from corrosion and/or degradation.

Turning now to components that can be used in electrodes of the present invention, electrodes of the present invention, in some embodiments, comprise a substrate. In some embodiments, a substrate comprises silicon carbide doped with titanium. In other embodiments, a substrate comprises $La_{1-x}Sr_xMnO_3$ [lanthanum strontium doped manganite (LSM)]. In another embodiment, a substrate comprises porous steel alloys. In one embodiment, a porous steel alloy comprises steel alloy 52. In some embodiments, a porous steel alloy suitable for use as an electrode substrate comprises steel alloy 316, stainless steel alloy 430, Crofer 22 APU®(Thyssen Krupp), E-Brite® (Alleghany Ludlum), HASTELLOY® C-276, INCONEL® 600, or HASTELLOY® X, each of which is commercially available from Mott Corporation of Farmington, Conn. In a further embodiment, a substrate comprises any metal or alloy known to one of skill in the art operable to serve as an electrode. Some embodiments of the present invention provide electrode substrates comprising at least one metal, at least one metal carbide, or a combination thereof. In some of those embodiments, the electrode substrate material may have electrical, structural, and mechanical properties that are better than those of ceramic electrodes.

Electrode substrates, according to further embodiments of the present invention, are porous. In some embodiments, a substrate has a porosity ranging from about 5% to about 40%. In another embodiment, a substrate has a porosity ranging from about 10% to about 30% or from about 15% to about 25%. In a further embodiment, a substrate has a porosity greater than about 40%. A substrate, in some embodiments, has a porosity ranging from about 40% to about 60%. In one embodiment, a substrate has a porosity greater than about 60%.

In addition to a substrate, some electrodes of the present invention optionally comprise a coating disposed on the substrate, the coating comprising at least one layer of at least one metal oxide. In some embodiments, a coating disposed on the substrate comprises a plurality of layers comprising one or more metal oxides. Metal oxide layers suitable for use in electrodes of the present invention can comprise any of the metal oxides recited herein, including cerium samarium oxides. Some embodiments of the present invention provide at least one metal oxide coating disposed on the electrode substrate that can act as an electrolyte, an electrode-electrolyte transition layer, a concentration-gradient layer, a matching layer for coefficients of thermal expansion, an electrical insulator, or a combination thereof, among other functions.

Substrate coatings comprising one or more metal oxide layers, according to some embodiments of the present invention, are porous. In one embodiment, a coating has a porosity ranging from about 5% to about 40%. In another embodiment, a coating has a porosity ranging from about 10% to about 30% or from about 15% to about 25%. In a further embodiment, a substrate coating has a porosity greater than about 40%. A substrate coating, in some embodiments, has a porosity ranging from about 40% to about 60%. In one embodiment, a substrate coating has a porosity greater than about 60%.

Substrate coatings can have any desired thickness. In one embodiment a substrate coating has a thickness ranging from about 1 nm to about 1 micron. In another embodiment, a substrate coating has a thickness ranging from about 50 nm to about 750 µm, from about 500 nm to about 500 µm, from about 1 µm to about 350 µm, or from about 10 µm to about 200 µm. In a further embodiment, a substrate coating has a thickness ranging from about 50 µm to about 100 µm. In some embodiments wherein a coating comprises a plurality of metal oxide layers, each metal oxide layer has a thickness ranging from about 5 nm to about 15 nm, wherein the total thickness of the coating is the summation of the thicknesses of the individual layers.

In some embodiments of electrodes of the present invention, a substrate-coating transition layer is interposed between the substrate and the coating. A substrate-coating transition layer comprises both substrate and coating materials. By comprising both substrate and coating materials, the substrate-coating transition layer, in some embodiments, is operable to reduce disparities in coefficients of thermal expansion between the substrate and the metal oxide coating of the electrode. Reducing such disparities can have an inhibitory effect on degradative pathways such as cracking or delamination between the substrate and metal oxide coating. Moreover, a substrate-coating transition layer provides increased stability by anchoring the metal oxide coating to the electrode.

In some embodiments, a substrate-coating transition layer has a thickness ranging from about 3 nm to about 100 nm or from about 20 nm to about 80 nm. In another embodiment, a substrate-coating transition layer has a thickness ranging from about 30 nm to about 60 nm or from about 40 nm to about 50 nm. In a further embodiment, a substrate-coating transition layer has a thickness less than about 10 nm or greater than about 100 nm.

Electrodes, according to some embodiments of the present invention, further comprise catalytic materials. Catalytic materials can comprise transition metals including, but not limited to, platinum, palladium, rhodium, nickel, cerium, gold, silver, zinc, lead, ruthenium, rhenium, or mixtures thereof. Catalytic materials, in some embodiments, are disposed in one or a plurality of metal oxide layers coating the substrate of an electrode. The combination of a metal oxide with pure metals or alloys, in some embodiments, produces a cermet. Electrodes of solid oxide fuel cells further comprising catalytic materials can function as fuel reformers operable to convert hydrocarbon fuels into hydrogen for subsequent use in the solid oxide fuel cell, in some embodiments. Moreover, electrodes further comprising catalytic materials can function as fuel reformers upstream and independent from the solid oxide fuel cell in other embodiments.

Electrodes comprising catalytic materials can additionally demonstrate compositional gradients based on the distribution of the catalytic materials in the plurality of metal oxide layers. In one embodiment, an electrode comprises a substrate and a plurality of metal oxide layers disposed on the substrate, wherein metal oxide layers proximal to the substrate comprise greater amounts of catalytic material than metal oxide layers distal to the substrate. Moreover, in another embodiment, metal oxide layers distal to the substrate comprise greater amounts of catalytic material than metal oxide layers proximal to the substrate. In one embodiment, for example, metal oxide layers distal to the substrate comprise about 5 weight percent catalytic material while metal oxide layers proximal to the substrate comprise about 1 weight percent catalytic material.

VI. Interconnects of Solid Oxide Cells

In another aspect, the present invention provides interconnects operable to be used in solid oxide cells as well as other applications. Interconnects of the present invention, in some embodiments, are resistant to harsh environments and chemical species which can degrade the interconnects. In one embodiment, the present invention provides an interconnect comprising a substrate comprising a first material, a coating composition comprising at least one layer of at least one metal oxide disposed on the substrate, and a substrate-coating transition layer interposed between the substrate and the coating. In some embodiments, a coating composition comprises a plurality of metal oxide layers. One or a plurality of metal oxide coatings can assist in protecting a metallic or ceramic interconnect substrate from degradative conditions and/or chemical species.

Turning now to components that can be used in various applications of the present invention, interconnects, in some embodiments, comprise substrates. In some embodiments, substrates comprise metal oxides including, but not limited to, lanthanum and yttrium chromites. In other embodiments, a substrate comprises metals or alloys, such as chromium based alloys. In one embodiment, a chromium based alloy comprises 5 weight percent iron and 1 weight percent yttria. In another embodiment, a substrate comprises at least one ferritic steel. In a further embodiment, a substrate comprises any metal operable to sufficiently transfer charge carriers into or from an external circuit. Thus, in some embodiments, interconnects of the present invention are adaptable to provide electrical communication between at least one electrode and an external circuit. In further embodiments, interconnects are adaptable to provide material communication between at least one electrode and an external source of at least one material, and/or at least one exit for at least one material. For example, an interconnect can provide air or oxygen to the cathode of a solid oxide fuel cell. For another example, an interconnect can provide an exhaust conduit for water or steam to exit a solid oxide fuel cell. For yet another example, an interconnect can provide a conduit to a storage system for hydrogen generated at the cathode of a solid oxide electrolyzer cell. In still other embodiments, an interconnect provides both electrical and material communication between at least one electrode and an external circuit and external sources and/or reservoirs and/or exhaust for material. Optionally, an interconnect may be adapted to provide thermal communication between an electrode and an external source or sink for thermal energy.

Accordingly, interconnects can have any desired shape. Wires, films, monoliths, porous monoliths, disks, tubes, pipes, among other shapes, are possible. Connections between an interconnect and an electrode can adopt any suitable form. In some embodiments, the same piece of metal (or metal carbide, cermet, or other material) forms the substrate for the electrode and for the interconnect; in such embodiments, the portion of the metal that engages in the electrochemical reaction in the cell is the electrode portion, while the portion of the metal providing communication outside the cell is the interconnect portion. In other embodiments, electrical contact between the interconnect and the electrode are made with any suitable connection, such as, for example, welding, stamping, melt fusion, mechanical connections such as bolts or rivets, conductive paints such as silver paint, sputtered metals, and conductive adhesives, as well as combinations thereof. Such connections can be made before, during, or after formation of metal oxides as described herein.

Interconnect substrates can have any desired thickness. In one embodiment a substrate has a thickness ranging from about 1 nm to about 1 mm. In another embodiment, a substrate has a thickness ranging from about 50 nm to about 750 μm, from about 500 nm to about 500 μm, from about 1 μm to about 350 μm, or from about 10 μm to about 200 μm. In a further embodiment, a substrate has a thickness ranging from about 50 μm to about 100 μm.

In addition to a substrate, an interconnect of some embodiments of the present invention comprises a coating disposed on the substrate, the coating comprising at least one layer of at least one metal oxide. In some embodiments, a coating disposed on the substrate comprises a plurality of layers comprising one or more metal oxides. Metal oxide layers suitable for use in interconnects of the present invention can comprise any of the metal oxides recited herein, such as, for example, any of the cerium samarium oxides.

Substrate coatings comprising one or more metal oxide layers, according to some embodiments of the present invention, are porous. In one embodiment, a coating has a porosity ranging from about 5% to about 40%. In another embodiment, a coating has a porosity ranging from about 10% to about 30% or from about 15% to about 25%. In a further embodiment, a substrate coating has a porosity greater than about 40%. A substrate coating, in some embodiments, has a porosity ranging from about 40% to about 60%. In one embodiment, a substrate coating has a porosity greater than about 60%.

Substrate coatings can have any desired thickness. In one embodiment, a substrate coating has a thickness ranging from about 1 nm to about 1 micron. In another embodiment, a substrate coating has a thickness ranging from about 50 nm to about 750 μm, from about 500 nm to about 500 μm, from about 1 μm to about 350 μm, or from about 10 μm to about 200 μm. In a further embodiment, a substrate coating has a thickness ranging from about 50 μm to about 100 μm. In some embodiments wherein a coating comprises a plurality of metal oxide layers, each metal oxide layer has a thickness ranging from about 5 nm to about 15 nm, wherein the total thickness of the coating is the summation of the thicknesses of the individual layers.

In some embodiments of interconnects of the present invention, a substrate-coating transition layer is interposed between the substrate and the coating. A substrate-coating transition layer comprises both substrate and coating materials. By comprising both substrate and coating materials, the substrate-coating transition layer, in some embodiments, is operable to reduce disparities in coefficients of thermal expansion between the substrate and the metal oxide coating of the interconnect. Reducing such disparities can have an inhibitory effect on degradative pathways such as cracking or delamination between the substrate and metal oxide coating. Moreover, a substrate-coating transition layer provides increased stability by anchoring the metal oxide coating to the electrode.

In some embodiments, a substrate-coating transition layer of an interconnect has a thickness ranging from about 3 nm to about 100 nm or from about 20 nm to about 80 nm. In another embodiment, a substrate-coating transition layer has a thickness ranging from about 30 nm to about 60 nm or from about 40 nm to about 50 nm. In a further embodiment, a substrate-coating transition layer has a thickness less than about 10 nm or greater than about 100 nm.

Additionally, in order to reduce problems and disadvantages associated with variances in coefficients of thermal expansion between interconnects and electrodes of solid oxide cells, interconnects, in some embodiments of the present invention, comprise compositional gradients. An interconnect, in one embodiment, comprises a region proximal to a cathode and a region distal to the cathode, wherein the region proximal to the cathode has a greater amount of cathode material than the region of the interconnect distal from the cathode. Moreover, in another embodiment, an interconnect comprises a region proximal to an anode and a region distal to the anode, wherein the region proximal to the anode has a greater amount of anode material than the region of the interconnect distal from the anode.

In another embodiment, an interconnect comprises a substrate coated with a plurality of metal oxide layers. Layers of the interconnect proximal to the cathode comprise greater amounts of cathode material than layers of the interconnect distal from the cathode. Moreover, in another embodiment, layers of the interconnect proximal to the anode comprise greater amounts of anode material than layers of the interconnect distal from the anode.

VII. Methods of Making Solid Oxide Cells

In another aspect, the present invention provides methods of making solid oxide cells. In one embodiment, a method of making a solid oxide cell comprises providing a first electrode, applying a metal compound composition to the first electrode, and converting at least some of the metal compound composition to a metal oxide composition. In some embodiments, the metal compound composition is fully converted to a metal oxide composition. A metal compound composition comprises at least one metal-containing compound that can be at least partially converted to at least one metal oxide. In some embodiments, the metal compound composition comprises at least one metal carboxylate, at least one metal alkoxide, at least one metal β-diketonate, or a combination thereof.

A metal carboxylate comprises the metal salt of a carboxylic acid, e.g., at least one metal atom and at least one carboxylate moiety. In some embodiments of the methods of the present invention, a metal salt of a carboxylic acid comprises a transition metal salt. In other embodiments, a metal salt of a carboxylic acid comprises a rare earth metal salt. In a further embodiment, metal carboxylate compositions comprise a plurality of metal salts of carboxylic acids. In one embodiment, a plurality of metal salts comprises at least one rare earth metal salt of a carboxylic acid and at least one transition metal salt of a carboxylic acid.

Metal carboxylates can be produced by a variety of methods known to one skilled in the art. Non-limiting examples of methods for producing the metal carboxylate are shown in the following reaction schemes:

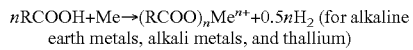
$n$RCOOH+Me→(RCOO)$_n$Me$^{n+}$+0.5$n$H$_2$ (for alkaline earth metals, alkali metals, and thallium)

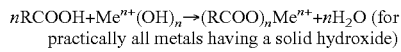
$n$RCOOH+Me$^{n+}$(OH)$_n$→(RCOO)$_n$Me$^{n+}$+$n$H$_2$O (for practically all metals having a solid hydroxide)

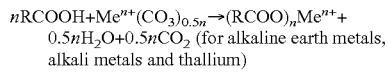
$n$RCOOH+Me$^{n+}$(CO$_3$)$_{0.5n}$→(RCOO)$_n$Me$^{n+}$+ 0.5$n$H$_2$O+0.5$n$CO$_2$ (for alkaline earth metals, alkali metals and thallium)

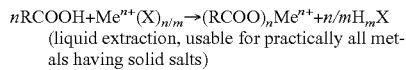
$n$RCOOH+Me$^{n+}$(X)$_{n/m}$→(RCOO)$_n$Me$^{n+}$+$n/m$H$_m$X (liquid extraction, usable for practically all metals having solid salts)

In the foregoing reaction schemes, X is an anion having a negative charge m, such as,
e.g., halide anion, sulfate anion, carbonate anion, phosphate anion, among others; n is a positive integer; and Me represents a metal atom. R in the foregoing reaction schemes can be chosen from a wide variety of radicals. Suitable carboxylic acids for use in making metal carboxylates include, for example:
Monocarboxylic Acids:

Monocarboxylic acids where R is hydrogen or unbranched hydrocarbon radical, such as, for example, HCOOH-formic, CH$_3$COOH-acetic, CH$_3$CH$_2$COOH-propionic, CH$_3$CH$_2$CH$_2$COOH(C$_4$H$_8$O$_2$)-butyric, C$_5$H$_{10}$O$_2$-valeric, C$_6$H$_{12}$O$_2$-caproic, C$_7$H$_{14}$-enanthic; further: caprylic, pelargonic, undecanoic, dodecanoic, tridecylic, myristic, pentadecylic, palmitic, margaric, stearic, and nonadecylic acids;

Monocarboxylic acids where R is a branched hydrocarbon radical, such as, for example, (CH$_3$)$_2$CHCOOH-isobutyric, (CH$_3$)$_2$CHCH$_2$COOH-3-methylbutanoic, (CH$_3$)$_3$CCOOH-trimethylacetic, including VERSATIC 10 (trade name) which is a mixture of synthetic, saturated carboxylic acid isomers, derived from a highly-branched C$_{10}$ structure;

Monocarboxylic acids in which R is a branched or unbranched hydrocarbon radical containing one or more double bonds, such as, for example, CH$_2$=CHCOOH-acrylic, CH$_3$CH=CHCOOH-crotonic, CH$_3$(CH$_2$)$_7$CH=CH(CH$_2$)$_7$COOH-oleic, CH$_3$CH=CHCH=CHCOOH-hexa-2,4-dienoic, (CH$_3$)$_2$C=CHCH$_2$CH$_2$C(CH$_3$)=CHCOOH-3,7-dimethylocta-2,6-dienoic, CH$_3$(CH$_2$)$_4$—CH=CHCH$_2$CH=CH(CH$_2$)$_7$COOH-linoleic, further: angelic, tiglic, and elaidic acids;

Monocarboxylic acids in which R is a branched or unbranched hydrocarbon radical containing one or more triple bonds, such as, for example, CH≡CCOOH-propiolic, CH$_3$C≡CCOOH-tetrolic, CH$_3$(CH$_2$)$_4$C≡CCOOH-oct-2-ynoic, and stearolic acids;

Monocarboxylic acids in which R is a branched or unbranched hydrocarbon radical containing one or more double bonds and one or more triple bonds;

Monocarboxylic acids in which R is a branched or unbranched hydrocarbon radical containing one or more double bonds and one or more triple bonds and one or more aryl groups;

Monohydroxymonocarboxylic acids in which R is a branched or unbranched hydrocarbon radical that contains one hydroxyl substituent, such as, for example, HOCH$_2$COOH-glycolic, CH$_3$CHOHCOOH-lactic, C$_6$H$_5$CHOHCOOH-amygdalic, and 2-hydroxybutyric acids;

Dihydroxymonocarboxylic acids in which R is a branched or unbranched hydrocarbon radical that contains two hydroxyl substituents, such as, for example, (HO)$_2$CHCOOH-2,2-dihydroxyacetic acid;

Dioxycarboxylic acids, in which R is a branched or unbranched hydrocarbon radical that contains two oxygen atoms each bonded to two adjacent carbon atoms, such as, for example, C$_6$H$_3$(OH)$_2$COOH-dihydroxy benzoic, C$_6$H$_2$(CH$_3$)(OH)$_2$COOH-orsellinic; further: caffeic, and piperic acids;

Aldehyde-carboxylic acids in which R is a branched or unbranched hydrocarbon radical that contains one aldehyde group, such as, for example, CHOCOOH-glyoxalic acid;

Keto-carboxylic acids in which R is a branched or unbranched hydrocarbon radical that contains one ketone group, such as, for example, CH$_3$COCOOH-pyruvic, CH$_3$COCH$_2$COOH-acetoacetic, and CH$_3$COCH$_2$CH$_2$COOH-levulinic acids;

Monoaromatic carboxylic acids, in which R is a branched or unbranched hydrocarbon radical that contains one aryl substituent, such as, for example, C$_6$H$_5$COOH-benzoic, C$_6$H$_5$CH$_2$COOH-phenylacetic, C$_6$H$_5$CH(CH$_3$)COOH-2-phenylpropanoic, C$_6$H$_5$CH=CHCOOH-3-phenylacrylic, and C$_6$H$_5$C≡CCOOH-3-phenyl-propiolic acids;
Multicarboxylic Acids:

Saturated dicarboxylic acids, in which R is a branched or unbranched saturated hydrocarbon radical that contains one carboxylic acid group, such as, for example, HOOC—COOH-oxalic, HOOC—CH$_2$—COOH-malonic, HOOC—(CH$_2$)$_2$—COOH-succinic, HOOC—(CH$_2$)$_3$—COOH-glutaric, HOOC—(CH$_2$)$_4$—COOH-adipic; further: pimelic, suberic, azelaic, and sebacic acids;

Unsaturated dicarboxylic acids, in which R is a branched or unbranched hydrocarbon radical that contains one carboxylic acid group and at least one carbon-carbon multiple bond, such as, for example, HOOC—CH=CH—COOH-fumaric; further: maleic, citraconic, mesaconic, and itaconic acids;

Polybasic aromatic carboxylic acids, in which R is a branched or unbranched hydrocarbon radical that contains at least one aryl group and at least one carboxylic acid group, such as, for example, C$_6$H$_4$(COOH)$_2$-phthalic (isophthalic, terephthalic), and C$_6$H$_3$(COOH)$_3$-benzyl-tri-carboxylic acids;

Polybasic saturated carboxylic acids, in which R is a branched or unbranched hydrocarbon radical that contains at least one carboxylic acid group, such as, for example, ethylene diamine N,N'-diacetic acid, and ethylene diamine tetraacetic acid (EDTA);
Polybasic Oxyacids:

Polybasic oxyacids, in which R is a branched or unbranched hydrocarbon radical containing at least one hydroxyl substituent and at least one carboxylic acid group, such as, for example, HOOC—CHOH—COOH-tartronic, HOOC—CHOH—CH$_2$—COOH-malic, HOOC—C(OH)=CH—COOH-oxaloacetic, HOOC—CHOH—CHOH—COOH-tartaric, and HOOC—CH$_2$—C(OH)COOH—CH$_2$COOH-citric acids.

A metal compound composition, in some embodiments of the present invention, comprises a solution of carboxylic acid salts of one or more metals ("metal carboxylate"). A liquid metal carboxylate composition can comprise a single metal, to form a single metal carboxylate, or a mixture of metals, to form a corresponding mixture of metal carboxylates. In addition, a liquid metal carboxylate composition can contain different carboxylate moieties. In some embodiments, a liquid metal carboxylate composition contains a mixture of metals, as these compositions form mixed oxides having various properties.

Solvent used in the production of liquid metal carboxylate compositions, in some embodiments, comprise an excess of the liquid carboxylic acid which was used to form the metal carboxylate salt. In other embodiments, a solvent comprises another carboxylic acid, or a solution of a carboxylic acid in another solvent, including, but not limited to, organic solvents such as benzene, toluene, xylene, chloroform, dichloromethane, or combinations thereof.

Carboxylic acids suitable for use generating liquid metal carboxylate compositions, in some embodiments, are those which: (1) can form a metal carboxylate, where the metal carboxylate is soluble in excess acid or another solvent; and (2) can be vaporized in a temperature range that overlaps with the oxide conversion temperature range.

In some embodiments, a carboxylic acid has a formula R—COOH, where R is alkyl, alkenyl, alkynyl or aryl.

In some embodiments, the monocarboxylic acid comprises one or more carboxylic acids having the formula I below:

$$R^{\circ}\text{—C}(R'')(R')\text{—COOH} \tag{I}$$

wherein:

$R^{\circ}$ is selected from H or $C_1$ to $C_{24}$ alkyl groups; and

R' and R" are each independently selected from H and $C_1$ to $C_{24}$ alkyl groups;

wherein the alkyl groups of $R^{\circ}$, R', and R" are optionally and independently substituted with one or more substituents, which are alike or different, chosen from hydroxy, alkoxy, amino, and aryl radicals, and halogen atoms.

The term alkyl, as used herein, refers to a saturated straight, branched, or cyclic hydrocarbon, or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl, heptyl, octyl, nonyl, and decyl.

The term alkoxy, as used herein, refers to a saturated straight, branched, or cyclic hydrocarbon, or a combination thereof, including $C_1$ to $C_{24}$, methyl, ethyl, n-propyl, isopropyl, n-butyl, isobutyl, t-butyl, n-pentyl, cyclopentyl, isopentyl, neopentyl, n-hexyl, isohexyl, cyclohexyl, 3-methylpentyl, 2,2-dimethylbutyl, 2,3-dimethylbutyl, heptyl, octyl, nonyl, and decyl, in which the hydrocarbon contains a single-bonded oxygen atom that can bond to or is bonded to another atom or molecule.

The terms alkenyl and alkynyl, as used herein, refer to a straight, branched, or cyclic hydrocarbon, including $C_1$ to $C_{24}$, with at least one double or triple bond, respectively.

Alkyl, alkenyl, alkoxy, and alkynyl radicals are unsubstituted or substituted with one or more alike or different substituents independently chosen from halogen atoms, hydroxy, alkoxy, amino, aryl, and heteroaryl radicals.

Moreover, the term aryl or aromatic, as used herein, refers to a monocyclic or bicyclic hydrocarbon ring molecule having conjugated double bonds about the ring. In some embodiments, the ring molecule has 5- to 12-members, but is not limited thereto. The ring may be unsubstituted or substituted having one or more alike or different independently-chosen substituents, wherein the substituents are chosen from alkyl, alkenyl, alkynyl, alkoxy, hydroxyl, and amino radicals, and halogen atoms. Aryl includes, for example, unsubstituted or substituted phenyl and unsubstituted or substituted naphthyl.

The term heteroaryl as used herein refers to a monocyclic or bicyclic aromatic hydrocarbon ring molecule having at least one heteroatom chosen from O, N, P, and S as a member of the ring, and the ring is unsubstituted or substituted with one or more alike or different substituents independently chosen from alkyl, alkenyl, alkynyl, hydroxyl, alkoxy, amino, alkylamino, dialkylamino, thiol, alkylthio, =O, =NH, =PH, =S, and halogen atoms. In some embodiments, the ring molecule has 5- to 12-members, but is not limited thereto.

The alpha branched carboxylic acids, in some embodiments, have an average molecular weight ranging from about 130 to 420 g/mol or from about 220 to 270 g/mol. The carboxylic acid may also be a mixture of tertiary and quaternary carboxylic acids of Formula I. VIK acids can be used as well. See U.S. Pat. No. 5,952,769, at col. 6, ll. 12-51, which patent is incorporated herein by reference in its entirety.

Either a single carboxylic acid or a mixture of carboxylic acids can be used to form the liquid metal carboxylate. In some embodiments, a mixture of carboxylic acids contains 2-ethylhexanoic acid wherein $R^{\circ}$ is H, R" is $C_2H_5$ and R' is $C_4H_9$, in the formula (I) above. The use of a mixture of carboxylates can provide several advantages. In one aspect, the mixture has a broader evaporation temperature range, making it more likely that the evaporation temperature of the acid mixture will overlap the metal carboxylate decomposition temperature, allowing the formation of a metal oxide coating. Moreover, the possibility of using a mixture of carboxylates avoids the need and expense of purifying an individual carboxylic acid.

Other metal compounds can be used to form metal oxides in accordance with the present invention. Such metal compounds can be used alone or in combination, or in combination with one or more metal carboxylates. Metal compounds other than carboxylates and those mentioned elsewhere include metal alkoxides and metal β-diketonates.

Metal alkoxides suitable for use in the present invention include at least one metal atom and at least one alkoxide radical —$OR^2$ bonded to the at least one metal atom. Such metal alkoxides include those of formula II:

$$M(OR^2)_z \tag{II}$$

in which M is a metal atom of valence z+;

z is a positive integer, such as, for example, 1, 2, 3, 4, 5, 6, 7, and 8;

$R^2$ can be alike or different and are independently chosen from unsubstituted and substituted alkyl, unsubstituted and substituted alkenyl, unsubstituted and substituted alkynyl, unsubstituted and substituted heteroaryl, and unsubstituted and substituted aryl radicals, wherein substituted alkyl, alkenyl, alkynyl, heteroaryl, and aryl radicals are substituted with one or more alike or different substituents independently chosen from halogen, hydroxy, alkoxy, amino, heteroaryl, and aryl radicals.

In some embodiments, z is chosen from 2, 3, and 4.

Metal alkoxides are available from Alfa-Aesar and Gelest, Inc., of Morrisville, Pa. Lanthanoid alkoxides such as those of Ce, Nd, Eu, Dy, and Er are sold by Kojundo Chemical Co., Saitama, Japan, as well as alkoxides of Al, Zr, and Hf, among others. See, e.g., http://www.kojundo.co.jp/English/Guide/material/lanthagen.html.

Examples of metal alkoxides useful in embodiments of the present invention include methoxides, ethoxides, propoxides, isopropoxides, and butoxides and isomers thereof. The alkoxide substituents on a give metal atom are the same or different. Thus, for example, metal dimethoxide diethoxide, metal methoxide diisopropoxide t-butoxide, and similar metal alkoxides can be used. Suitable alkoxide substituents also may be chosen from:

1. Aliphatic series alcohols from methyl to dodecyl including branched and isostructured.

2. Aromatic series alcohols: benzyl alcohol —$C_6H_5CH_2OH$; phenyl-ethyl alcohol-$C_8H_{10}O$; phenyl-propyl alcohol-$C_9H_{12}O$, and so on.

Metal alkoxides useful in the present invention can be made according to many suitable methods. One method includes converting the metal halide to the metal alkoxide in the presence of the alcohol and its corresponding base. For example:

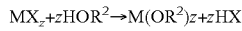

in which M, $R^2$, and z are as defined above for formula II, and X is a halide anion.

Metal β-diketonates suitable for use in the present invention contain at least one metal atom and at least one β-diketone of formula III as a ligand:

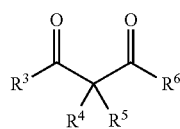

(III)

in which $R^3$, $R^4$, $R^5$, and $R^6$ are alike or different, and are independently chosen from hydrogen, unsubstituted and substituted alkyl, unsubstituted and substituted alkoxy, unsubstituted and substituted alkenyl, unsubstituted and substituted alkynyl, unsubstituted and substituted heteroaryl, unsubstituted and substituted aryl, carboxylic acid groups, ester groups having unsubstituted and substituted alkyl, and combinations thereof, wherein substituted alkyl, alkoxy, alkenyl, alkynyl, heteroaryl, and aryl radicals are substituted with one or more alike or different substituents independently chosen from halogen atoms, hydroxy, alkoxy, amino, heteroaryl, and aryl radicals.

It is understood that the β-diketone of formula III may assume different isomeric and electronic configurations before and while chelated to the metal atom. For example, the free β-diketone may exhibit enolate isomerism. Also, the β-diketone may not retain strict carbon-oxygen double bonds when the molecule is bound to the metal atom.

Examples of β-diketones useful in embodiments of the present invention include acetylacetone, trifluoroacetylacetone, hexafluoroacetylacetone, 2,2,6,6-tetramethyl-3,5-heptanedione, 6,6,7,7,8,8,8-heptafluoro-2,2-dimethyl-3,5-octanedione, ethyl acetoacetate, 2-methoxyethyl acetoacetate, benzoyltrifluoroacetone, pivaloyltrifluoroacetone, benzoylpyruvic acid, and methyl-2,4-dioxo-4-phenylbutanoate.

Other ligands are possible on the metal β-diketonates useful in the present invention, such as, for example, alkoxides such as —$OR^2$ as defined above, and dienyl radicals such as, for example, 1,5-cyclooctadiene and norbornadiene.

Metal β-diketonates useful in the present invention can be made according to any suitable method. β-diketones are well known as chelating agents for metals, facilitating synthesis of the diketonate from readily available metal salts.

Metal β-diketonates are available from Alfa-Aesar and Gelest, Inc. Also, Strem Chemicals, Inc. of Newburyport, Mass., sells a wide variety of metal β-diketonates on the internet at http://www.strem.com/code/template.ghc?direct=cvdindex.

In some embodiments, a metal compound composition contains one metal compound as its major component and one or more additional metal compounds which may function as stabilizing additives. Stabilizing additives, in some embodiments, comprise trivalent metal compounds. Trivalent metal compounds include, but are not limited to, chromium, iron, manganese and nickel carboxylates. A metal compound composition, in some embodiments, comprises both cerium and chromium carboxylates.

Metals suitable for use in forming metal compounds including, but not limited to liquid metal carboxylates, metal alkoxides, and metal β-diketonates comprise lithium, beryllium, sodium, magnesium, aluminum, silicon, potassium, calcium, scandium, titanium, vanadium, chromium, manganese, iron, cobalt, nickel, copper, zinc, gallium, germanium, arsenic, bromine, rubidium, strontium, yttrium, zirconium, niobium, molybdenum, technetium, ruthenium, rhodium, palladium, antimony, tellurium, silver, cadmium, indium, tin, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, irridium, gold, mercury, thallium, lead, bismuth, radium, actinium, platinum, thorium, protactinium, uranium, neptunium, plutonium, americium, berkelium, californium, einsteinium, fermium, mendelevium, nobelium, lawrencium, or curium. Any of the foregoing metals or combinations thereof can be used to form metal oxides according to embodiments of the present invention.

In some embodiments, the amount of metal forming the major component of the metal compound composition ranges from about 65 weight percent to about 97 weight percent or from about 80 weight percent to about 87 weight percent of the total metal in the compound composition. In other embodiments, the amount of metal forming the major component of the metal compound composition ranges from about 90 weight percent to about 97 weight percent of the total metal present in the compound composition. In a further embodiment, the amount of metal forming the major component of the metal compound composition is less than about 65 weight percent or greater than about 97 weight percent of the total metal present in the compound composition.

In some embodiments, metal compounds operable to function as stabilizing additives are present in amounts such that the total amount of the metal in metal compounds which are the stabilizing additives is at least 3% by weight of the total metal in the liquid metal compound composition.

The amount of metal in a liquid metal compound composition, according to some embodiments, ranges from about 20 to about 150 grams of metal per kilogram of liquid metal compound composition. In other embodiments, the amount of metal in a liquid metal compound composition ranges from about 30 to about 50 grams of metal per kilogram of liquid metal compound composition. In, a further embodiment, a liquid metal compound composition comprises from about 30 to about 40 grams of metal per kg of composition. In one embodiment, a metal amount is less than about 20 grams of metal per kilogram of liquid metal compound or greater than 150 grams of metal per kilogram of liquid metal compound.

Liquid metal compound compositions, in some embodiments of solid oxide cell production methods, further comprise one or more catalytic materials. Catalytic materials, in such embodiments, comprise transition metals including, but not limited to, platinum, palladium, rhodium, nickel, cerium, gold, silver, zinc, lead, ruthenium, rhenium, or mixtures thereof. Catalytic materials, in some embodiments, are present in liquid metal compound compositions in an amount ranging from about 0.5 weight percent to about 10 weight percent of the composition.

In other embodiments, liquid metal compound composition further comprises nanoparticles operable to alter the pore structure and porosity of the metal oxide resulting from the conversion of the liquid metal compound composition. Nanoparticles, in some embodiments, comprise metal oxide nanoparticles. Nanoparticles, in some embodiments, are present in liquid metal compound compositions in an amount ranging from about 0.5 percent by volume to about 30 percent by volume of the liquid metal compound composition. In another embodiment, nanoparticles are present in the liquid metal compound composition in an amount ranging from about 5 percent by volume to about 15 percent by volume of the liquid metal compound composition.

In addition to liquids, metal compound compositions, in some embodiments of methods of the present invention, comprise solid metal compound compositions, vapor metal compound compositions, or combinations thereof. In one embodiment, a solid metal compound composition comprises one or more metal compound powders. In another embodiment, a vapor metal compound composition comprises at least one gas phase metal compound operable to condense on a substrate prior to conversion to at least one metal oxide. In some embodiments, the substrate is cooled to enhance condensation of the vapor phase metal compound composition. In one embodiment, for example, a substrate such as a steel coupon is placed in a vacuum chamber, and the chamber is evacuated. Vapor of one or more metal compounds, such as cerium (IV) 2-hexanoate, enters the vacuum chamber and deposits on the steel substrate. Subsequent to deposition, the metal compound is exposed to conditions operable to convert the metal compound to a metal oxide. In a further embodiment, a metal compound composition comprises gels chosen from suitable gels including, but not limited to, sol-gels, hydrogels, and combinations thereof.

Applying a metal compound composition to the first electrode of a solid oxide cell can be accomplished by any suitable method, such as those known to one of skill in the art. In one embodiment, the first electrode is dipped into the liquid metal compound composition. In another embodiment, a swab, sponge, dropper, pipette, spray, brush or other applicator is used to apply the liquid metal compound composition to the first electrode. In some embodiments, a vapor phase metal compound composition is condensed on the first electrode. In other embodiments, lithographic methods can be used to apply the metal compound composition to the first electrode.

A metal compound composition, in some embodiments, is applied to the first electrode at a temperature less than about 250° C. In other embodiments, a metal compound composition is applied to the first electrode at a temperature less than about 200° C., less than about 150° C., less than about 100° C., or less than about 50° C. In a further embodiment, a metal compound composition is applied to the first electrode at room temperature.

An electrode, in some embodiments, is pretreated prior to application of the metal compound composition. In one embodiment, for example, the first electrode can be etched according to known methods, for example, with an acid wash comprising nitric acid, sulphuric acid, hydrochloric acid, phosphoric acid, or a combination thereof, or with a base wash comprising sodium hydroxide or potassium hydroxide, for example. In another embodiment, the first electrode is polished, with or without the aid of one or more chemical etching agents, abrasives, and polishing agents, to make the surface either rougher or smoother. In a further embodiment, the first electrode is pretreated such as by carburizing, nitriding, plating, or anodizing.

Following application, the metal compound composition is at least partially converted to a metal oxide. In some embodiments, the metal compound composition is fully converted to a metal oxide.

Converting a metal compound composition comprising at least one metal salt of a carboxylic acid, according to some embodiments of the present invention, comprises exposing the metal compound composition to an environment operable to convert the at least one metal salt to at least one metal oxide. Environments operable to convert metal compounds to metal oxides, in some embodiments, provide conditions sufficient to vaporize and/or decompose the compound moieties and precipitate metal oxide formation. In one embodiment, an environment operable to convert metal compounds to metal oxides comprises a heated environment. A metal salt of a carboxylic acid, for example, can be exposed to an environment heated to a temperature operable to convert the carboxylic acid and induce formation of the metal oxide. In some embodiments, the environment is heated to a temperature greater than about 400° C. In some embodiments, the environment is heated to a temperature up to about 425° C. or up to about 450° C. In other embodiments, the environment is heated to a temperature ranging from about 400° C. to about 650° C. In a further embodiment, the environment is heated to a temperature ranging from about 400° C. to about 550° C.

In some embodiments, the metal compound composition penetrates into the substrate of the first electrode to a depth ranging from about 10 nm to about 100 nm or from about 20 nm to about 80 nm. In other embodiments, the metal compound composition penetrates into the substrate of the first electrode to a depth ranging from about 30 nm to about 60 nm or from about 40 nm to about 50 nm. Converting the metal compound on the substrate of the first electrode to a metal oxide, in some embodiments, produces an electrode-electrolyte transition layer comprising electrolyte metal oxide material and electrode substrate material. In other embodiments, the metal compound composition does not penetrate into the porous structure of the electrolyte and an abrupt interface exists between the electrode and the electrolyte.

Moreover, exposing metal compound compositions to environments operable to convert the compositions to metal oxides, as provided herein, eliminates the need for sintering to produce metal oxides. By eliminating sintering, solid oxide cell production methods of the present invention gain several advantages. One advantage is that the lower temperatures of some methods of the present invention do not induce grain growth or other degradative processes in various layers of the solid oxide cell during production. Another advantage is that the compound compositions permit tailoring of individual metal oxide layers in the construction of electrolytes and electrodes. Methods of the present invention, for example, permit one metal oxide layer of an electrolyte or electrode to have completely different compositional and/or physical parameters in comparison to an adjacent metal oxide layer, in some embodiments. Such control over the construction of electrolytes and electrodes of solid oxide cells is extremely difficult and, in many cases, not possible with present sintering techniques.

In another embodiment, a method of making a solid oxide cell comprises providing a first electrode and depositing at least one electrolyte layer on the first electrode, wherein depositing at least one electrolyte layer comprises applying a metal compound composition to the first electrode, and converting at least some of the metal compound composition to a metal oxide. A metal compound composition can comprise a solid, liquid, or vapor metal compound composition as provided herein. In some embodiments, more than one metal compound composition is applied before conversion.

In some embodiments, a plurality of electrolyte layers are stacked on the first electrode. A method of producing a solid oxide cell, in one embodiment, comprises providing a first electrode and stacking a plurality of electrolyte layers on the first electrode, wherein each layer of electrolyte is stacked on a preceding layer by applying a metal compound composition to the preceding layer. The metal compound composition is subsequently converted to a metal oxide. In another embodiment, the repetition of multiple layers of electrolyte depositions is used to gradually add a particular nano-scale thickness of electrolyte onto the first electrode that serves, in this case, as the body or substrate for the deposited thin film of electrolyte. In one embodiment, the preceding layer comprises the first electrode. In another embodiment, the preceding layer comprises one of the plurality of electrolyte layers.

In some embodiments of methods for making solid oxide cells, a second electrode is deposited on the opposite surface of the electrolyte so that the electrolyte becomes the central layer between the two outer electrodes. The successive building up of thin film layers (from first electrode to electrolyte to second electrode) completes the construction of the solid oxide cell. In one embodiment, a second electrode is deposited on an electrolyte by applying a metal compound composition to the electrolyte, contacting the metal compound composition with the second electrode, and converting at least some of the metal compound composition to a metal oxide composition. In some embodiments, the metal compound composition is fully converted to a metal oxide.

Converting a metal compound composition comprising at least one metal salt of a carboxylic acid in the deposition of a second electrode, according to some embodiments of the present invention, comprises exposing the metal compound composition to an environment capable of converting at least one metal salt to at least one metal oxide as described herein. Converting other metal compositions, such as metal alkoxides, metal β-diketonates, combinations thereof, and combinations thereof including at least one metal carboxylate in some embodiments, also comprises exposing the metal composition to an environment capable of converting the metal compounds in the composition to at least one metal oxide.

The conversion environment, for various embodiments of the present invention, can be any suitable environment, and the conversion can be precipitated by any suitable means. In some embodiments of the present invention, the substrate is heated; in others, the atmosphere about the metal compound composition is heated; in still others, the metal compound composition is heated. In further embodiments, a substrate having a metal compound composition deposited thereon can be heated in an oven, or exposed to heated gas. The conversion environment may also be created using induction heating through means familiar to those skilled in the art of induction heating. Alternatively, the conversion environment may be provided using a laser applied to the surface area for sufficient time to allow at least some of the metal compounds to convert to metal oxides. In other applications, the conversion environment may be created using an infra-red light source which can reach sufficient temperatures to convert at least some of the metal compounds to metal oxides. Some embodiments may employ a microwave emission device to cause at least some of the metal compound to convert. Other embodiments provide a plasma to heat the metal compound. In the case of induction heating, microwave heating, lasers, plasmas, and other heating methods that can produce the necessary heat levels in a short time, for example, within seconds, 1 minute, 10 minutes, 20 minutes, 30 minutes, 40 minutes, or one hour.

VIII. Methods of Making Electrodes

In addition to solid oxide cells, the present invention provides methods of making electrodes. In one embodiment, a method of making an electrode comprises providing a substrate and depositing at least one metal oxide layer on the substrate wherein depositing comprises applying a metal compound composition to the substrate, and converting at least some of the metal compound composition to a metal oxide composition. In some embodiments, the metal compound composition is fully converted to at least one metal oxide.

In some embodiments, a plurality of metal oxide layers are deposited on the substrate. In one embodiment, for example, a method of making an electrode comprises depositing a plurality of metal oxide layers on the substrate, wherein each layer of metal oxide is deposited on a preceding layer by applying a metal compound composition to the preceding layer. The metal compound composition is subsequently converted to at least one metal oxide.

In some embodiments, the metal compound composition penetrates into the substrate to a depth ranging from about 3 nm to about 100 nm or from about 20 nm to about 80 nm. In other embodiments, the metal compound composition penetrates into the substrate to a depth ranging from about 30 nm to about 60 nm or from about 40 nm to about 50 nm. Converting the metal compound on the substrate to a metal oxide, in some embodiments, produces the substrate-coating transition layer comprising substrate material and metal oxide coating material. In some embodiments, the metal compound composition does not penetrate the substrate and an abrupt interface exists between the substrate and coating.

Metal compound compositions suitable for use in methods of making electrodes are consistent with any of the metal compound compositions described hereinabove for use in methods of making solid oxide cells. Moreover, metal compound compositions can be applied and converted to metal oxide compositions in any manner consistent with the same recited herein for methods of making solid oxide cells.

IX. Methods of Making Interconnects

In addition to solid oxide cells, the present invention provides methods of making interconnects. In one embodiment, a method of making an interconnect comprises providing a substrate and depositing at least one metal oxide layer on the substrate wherein depositing comprises applying a metal compound composition to the substrate, and converting at least some of the metal compound composition to a solid oxide composition. In some embodiments, the metal compound composition is fully converted to at least one metal oxide.

In some embodiments, a plurality of metal oxide layers are deposited on the substrate. In one embodiment, for example, a method of making an interconnect comprises depositing a plurality of metal oxide layers on the substrate, wherein each layer of metal oxide is deposited on a preceding layer by applying a metal compound composition to the preceding layer. That metal compound composition is subsequently converted to at least one metal oxide.

In some embodiments, the metal compound composition penetrates into the substrate to a depth ranging from about 3 nm to about 100 nm or from about 20 nm to about 80 nm. In other embodiments, the metal compound composition penetrates into the substrate to a depth ranging from about 30 nm to about 60 nm or from about 40 nm to about 50 nm. Converting the metal compound on the substrate to a metal oxide, in some embodiments, produces a substrate-coating transition layer comprising substrate material and metal oxide coating material. In some embodiments, the metal compound composition does not penetrate the porous structure of the substrate and an abrupt interface exists between the substrate and coating.

Metal compound compositions suitable for use in methods of making interconnects are consistent with any of the metal compound compositions described hereinabove for use in methods of making solid oxide cells. Moreover, metal compound compositions can be applied and converted to metal oxide compositions in any manner consistent with the same recited herein for methods of making solid oxide cells.

X. Methods of Increasing Ionic Conductivity and Triple Phase Boundaries

Through the greatly-increased thinness of the thin film electrolyte and through the extremely small size of the crystallites within the thin film electrolyte of some embodiments, the present invention allows for a solid electrolyte to be constructed that is both very conductive to ions (such as anionic oxygen)—and yet, to provide a thin film electrolyte that is sufficiently dense to act as the central barrier layer between, for example, the fuel electrode (anode) and the air electrode (cathode) of a solid oxide fuel cell.

The very thinness of the electrolyte (from 0.3 to 3.0 microns, in some embodiments) inherently allows for greater ionic conductivity of oxygen anions. Thus, the extremely small size of the crystallites may provide a greater density (and freedom from defects and pin-holes) that would be impossible were the crystallite size to be much larger.

In another aspect, the present invention provides methods of increasing the ionic conductivity of a solid electrolyte. A method of increasing the ionic conductivity of a solid electrolyte, in some embodiments, comprises increasing the number of grain boundaries in the solid electrolyte, wherein increasing the number of grain boundaries comprises forming a plurality of nanocrystalline grains comprising an electrolyte material. In some embodiments of the present invention, an electrolyte material comprises one or more metal oxides. Moreover, forming a plurality of metal oxide nanocrystalline grains comprises applying a metal compound composition to a substrate, and converting at least some of the metal compound composition to a plurality of metal oxide nanocrystalline grains. In some embodiments, ionic conductivity comprises oxygen ion conductivity.

In another aspect, the present invention provides methods of increasing the number of triple phase boundaries in a solid oxide cell comprising providing a solid electrolyte comprising a plurality of metal oxide nanocrystalline grains. Providing a solid electrolyte comprising a plurality of nanocrystalline grains, in some embodiments, comprises applying a metal compound composition to a substrate, and converting at least some of the metal compound composition to a plurality of metal oxide nanocrystalline grains. In some embodiments, the metal compound composition is fully converted into a plurality of metal oxide nanocrystalline grains. In one embodiment, the substrate comprises an electrode of the solid oxide cell.

In some embodiments of the present invention, nanocrystalline grains have an average size less than about 50 nm. In one embodiment, nanocrystalline grains of electrolyte layers have an average size ranging from about 1 nm to about 40 nm or from about 5 nm to about 30 nm. In another embodiment, nanocrystalline grains have an average size ranging from about 10 nm to about 25 nm. In a further embodiment, nanocrystalline grains have an average size less than about 10 nm or less than about 5 nm.

Metal compound compositions suitable for use in methods of increasing ionic conductivity and/or the number of triple phase boundaries are consistent with any of the metal compound compositions described hereinabove for use in methods of making solid oxide cells. Moreover, metal compound compositions can be applied and converted to metal oxide compositions in any manner consistent with the same recited herein for methods of making solid oxide cells.

XI. Methods of Reducing Differences in Coefficients of Thermal Expansion

In a further aspect, the present invention provides methods of reducing differences in coefficients of thermal expansion between an electrode and a solid electrolyte of a solid oxide cell. In one embodiment, a method of reducing differences in coefficients of thermal expansion between an electrode and a solid electrolyte comprises interposing an electrode-electrolyte transition layer between the electrode and the solid electrolyte. Interposing an electrode-electrolyte transition layer between the electrode and the solid electrolyte comprises applying an electrolyte composition comprising a metal compound composition to the electrode, and converting at least some of the metal compound to at least one metal oxide.

Metal compound compositions suitable for use in methods of reducing differences in coefficients of thermal expansion between an electrode and a solid electrolyte of a solid oxide cell are consistent with any of the metal compound compositions described hereinabove for use in methods of making solid oxide cells. Moreover, metal compound compositions can be applied and converted to metal oxide compositions in any manner consistent with the same recited herein for methods of making solid oxide cells.

XII. Application of Metal Layers

In some embodiments of solid oxide cells, electrodes, and/or interconnects of the present invention, metal layers, as opposed to metal oxide layers, are produced. In one embodiment, a method of producing a metal layer comprises providing a substrate and depositing at least one metal layer on the substrate wherein depositing comprises applying a metal compound composition to the substrate, and converting at least some of the metal compound composition to a metal layer. In some embodiments, the metal compound composition is fully converted to a metal layer. Converting the metal compound composition to a metal layer, in some embodiments, comprises exposing the metal compound composition to an environment operable to convert the at least one metal salt to a metal. Environments operable to convert metal compounds to a metal layer, in some embodiments, comprise reducing environments including, but not limited to, a hydrogen atmosphere ranging from 200° C. to 1200° C. or higher. Additional reducing environments known to one of skill in the art also are contemplated. In further embodiments, the at least one metal compound is converted into at least one metal oxide, which is then exposed to a reducing environment and at least partially converted into at least one metal. In still further embodiments, a contiguous metal layer forms, while in other embodiments, non-contiguous metal sites appear. In some embodiments, a substrate comprises a metal. In other embodiments, a substrate comprises a metal oxide, such as a metal oxide layer. In still other embodiments, a substrate comprises some other material, such as, for example, one or more polymers, ceramics, composites, cermets, or a combination thereof.

XIII. Methods of Generating Electric Current

In yet another aspect, the present invention provides a method of generating electric current comprising providing a solid oxide fuel cell comprising an air electrode, a fuel electrode, an electrolyte interposed between the air electrode and the fuel electrode, and at least one electrode-electrolyte transition layer; providing a fuel to the fuel electrode; providing oxygen to the air electrode; oxidizing the fuel to generate free electrons; transporting the free electrons through an external circuit to the air electrode (cathode); and then reducing the diatomic oxygen molecules at the air electrode to oxygen anions. In some embodiments, the fuel comprises hydrogen. In other embodiments, the fuel comprises at least one hydrocarbon. In embodiments wherein the fuel is a hydrocarbon, methods of generating electrical current further comprise reforming the hydrocarbon fuel at the fuel electrode.

Figure 2:
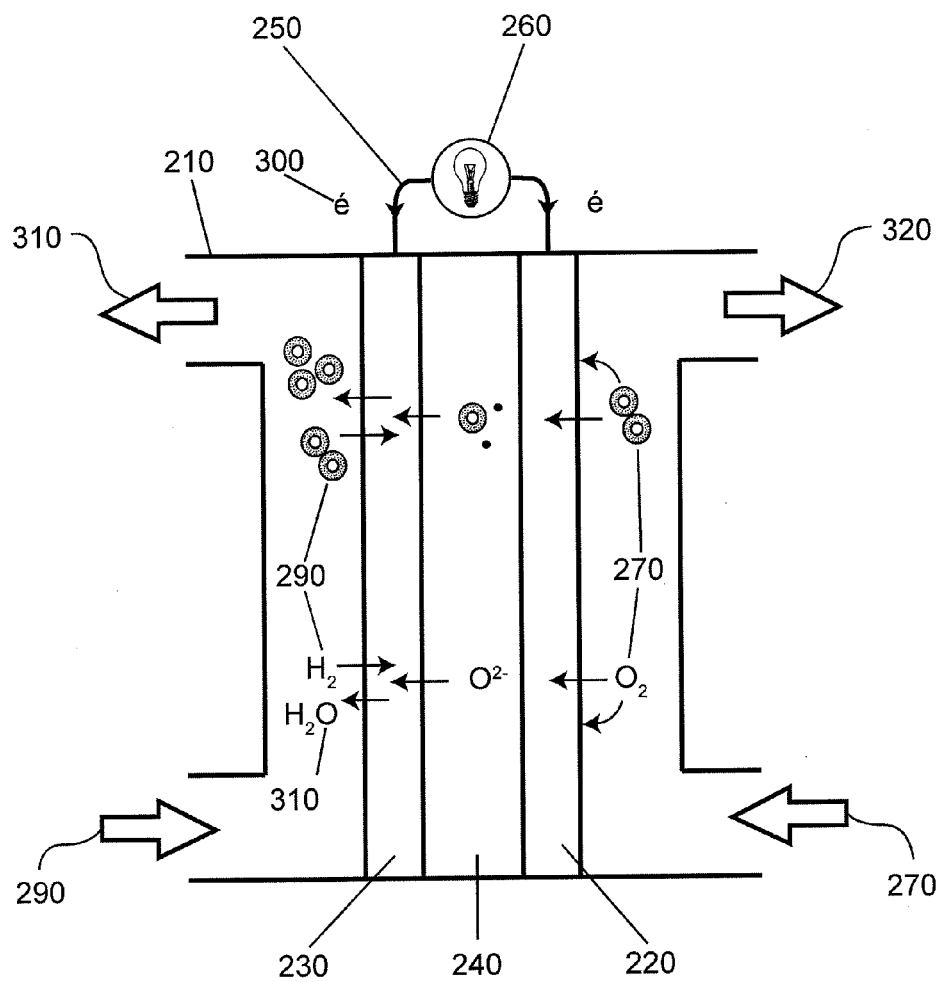
FIG. 2 illustrates a solid oxide fuel cell according to one embodiment of the present invention.

FIG. 2 illustrates a solid oxide fuel cell according to one embodiment of the present invention. As displayed in FIG. 2, the solid oxide fuel cell (210) comprises an air electrode (cathode) (220), a fuel electrode (anode) (230), an electrolyte (240) interposed between the air electrode (cathode) (220) and the fuel electrode (anode) (240). An electrode-electrolyte transition layer (not shown) is interposed between the air electrode (cathode) (220) and the electrolyte (240). The air electrode (cathode) (220) and the fuel electrode (anode) (230) are connected by an external circuit (250) across which a load (260) is applied. Oxygen ($O_2$) (270) or a mixture of gases comprising oxygen (e.g., air) is fed to the air electrode (220) wherein oxygen molecules (270) are reduced to oxygen anions ($O^{2-}$) (280). Moreover, hydrogen molecules ($H_2$) (290) from a fuel source are oxidized at the fuel electrode (230). Electrons (300) removed from hydrogen molecules (290) at the fuel electrode (230) travel through the external circuit (250) to the air electrode (cathode) (220) generating electric current while oxygen anions ($O^{2-}$) (280) travel through the electrolyte (240) to combine with hydrogen cations ($H^+$) (not shown) thereby producing water ($H_2O$) (310). Unused oxygen (320) exits the cell (210) after passing through the air electrode (220), while water (310) exits the cell (210) from the fuel electrode (230).

In other embodiments of the present invention, various configurations of fuel cells are contemplated. For example, more than one fuel electrode can pair with more than one air electrode. The physical configuration of the various electrodes, electrolytes, interconnects, and/or other components is not limited. In some embodiments, the configuration is optimized for size, current density, voltage, portability, fuel versatility, energy conservation, specific application, aesthetics, other considerations, or combinations thereof.

EXAMPLE 1

LSM Electrode

LSM planar electrodes can be purchased or formed as follows. LSM powder, available from American Elements (www.AmericanElements.com) is mixed with 5-10% wt. corn starch, compression molded into a flat disk shape not less than about 1/16th of an inch, and sintered at 1200° C. for 30 minutes in air. The resulting porous material is suitable for use as a cathode in a fuel cell embodying aspects of the present invention.

A two-inch diameter, approximately 2 mm thick LSM disc having an average pore size of about 15 μm and porosity of about 30% was formed in accordance with the foregoing procedure and polished with diamond paste to a roughness of approximately 1 μm. The polished surface was held against a 0.1 L volume vacuum chamber opening with an O-ring, and a vacuum was applied to measure the rate at which vacuum is lost through the porous electrode. A pressure of no less than 1200 mtorr was measured in the vacuum chamber, whereupon a valve between the vacuum chamber and a vacuum pump was closed. The pressure in the vacuum chamber returned rapidly to ambient pressure. See Table 1.

EXAMPLE 2

First Five Layers of YSZ Electrolyte with YSZ Nanoparticles and Powder

A viscous composition was made as follows. First, a liquid composition containing yttrium (III) 2-ethylhexanoate (15 molar % based on Y) and zirconium (IV) 2-ethylhexanoate (85 molar % based on Zr) was made. Then, one part of the liquid composition by weight was mixed with one part of YSZ nanoparticles having an average particle size of 50-100 nm; one part of the liquid composition was mixed with one part of YSZ powder having an average particle size of about 1 μm; and one part of the liquid composition was mixed with one part of YSZ powder having an average particle size of about 45 μm. All three mixtures were combined to form the viscous composition.

The LSM electrode from Example 1 was wetted on the polished surface with the viscous composition. The wet electrode was placed in a room-temperature electric furnace in air and the oven was heated to 450° C. Once the oven reached 450° C. in about 15 minutes, the oven was turned off, taking another 15 minutes to cool back to room temperature. The cooled electrode, now coated with a layer of YSZ electrolyte was subjected to the vacuum loss test described in Example 1. Without wishing to be bound by theory, it is believed that including the YSZ nanoparticles and powder in the composition applied to the surface of the electrode helps close the pores at the surface of the electrode.

Four more layers of the YSZ electrolyte with the YSZ nanoparticles and powder were formed by applying the viscous composition to the cooled electrode, heating and cooling the electrode as described above, and repeating. After each applying, heating and cooling, the electrode was subjected to the vacuum loss test described in Example 1.

EXAMPLE 3

Subsequent Layers of YSZ Electrolyte

The room-temperature electrode of Example 2 was coated repeatedly with a liquid composition containing yttrium (III) 2-ethylhexanoate (15 molar % based on Y) and zirconium (IV) 2-ethylhexanoate (85 molar % based on Zr) (and no nanoparticles or powder). After each application of the liquid composition, the electrode was heated and cooled as described in Example 2, and tested for vacuum loss as described in Example 1.

TABLE 1

Vacuum Loss Data

| Number of Coats | Pressure (mtorr) | Time to Equal Pressure (s) | Leak Rate (L * Torr/s) |
|---|---|---|---|
| 0 | 1200 | n/a | n/a |
| 1 | 800 | n/a | n/a |
| 2 | 750 | 7 | 1.09E+01 |
| 3 | 675 | 23 | 3.30E+00 |
| 4 | 600 | 30 | 2.53E+00 |
| 5 | 550 | 25 | 3.04E+00 |
| 6 | 600 | 30 | 2.53E+00 |
| 7 | 500 | 33 | 2.30E+00 |
| 8 | 400 | 47 | 1.62E+00 |
| 9 | 300 | 83 | 9.16E-01 |
| 10 | 260 | 105 | 7.24E-01 |
| 11 | 200 | 132 | 5.76E-01 |
| 12 | 155 | 180 | 4.22E-01 |
| 13 | 145 | 225 | 3.38E-01 |
| 14 | 150 | 180 | 4.22E-01 |
| 15 | 145 | 645 | 1.18E-01 |
| 16 | 130 | 705 | 1.08E-01 |
| 17 | 120 | 3240 | 2.35E-02 |
| 18 | 110 | 2880 | 2.64E-02 |
| 19 | 93 | 3300 | 2.30E-02 |
| 20 | 70 | 10320 | 7.36E-03 |

EXAMPLE 4

Extrapolation

Using the leakage rates measured in Table 1, it is possible to extrapolate the leakage rates to hypothetical samples having more coats of YSZ electrolyte. Table 2 shows estimated time for one pound of Freon ($CCl_2F_2$) to leak through YSZ-coated LSM samples having the same leakage rate behavior as the electrode prepared in Examples 1-3.

TABLE 2

Extrapolation for Freon Leakage

| Number of Coats | Leak Rate (L * torr/s) | Time for 1 lb. Freon to leak |
|---|---|---|
| 15 | 1.00E−01 | 10 days |
| 21 | 1.00E−02 | 3 months |
| 27 | 1.00E−03 | 2.7 years |
| 33 | 1.00E−04 | 27 years |
| 39 | 1.00E−05 | 270 years |
| 46 | 1.00E−06 | 2,700 years |
| 52 | 1.00E−07 | 27,000 years |
| 58 | 1.00E−08 | 270,000 years |
| 64 | 1.00E−09 | 2,700,000 years |
| 70 | 1.00E−10 | 27,000,000 years |

From the foregoing data, it is believed that approximately thirty coats of YSZ electrolyte applied as set forth in Examples 1-3 should be sufficient for certain solid oxide cell embodiments of the present invention. Other embodiments may require more or fewer coats. Still other embodiments may tolerate faster, or require slower, leak rates.

EXAMPLE 5

Forming Solid Oxide Fuel Cell

An electrode having several coats of electrolyte as made according to Examples 1-3 can be assembled into a cell with a porous nickel-YSZ cermet electrode. The Ni-YSZ electrode can be purchased or manufactured as explained in Example 1. Ni-YSZ cermet powders are also available from American Elements. A Ni-YSZ disk having 2" diameter and approximately 2 mm thickness can be placed onto a LSM disk having 20-40 layers of YSZ electrolyte coated thereon as described in Examples 2-3, along with an application of the liquid composition described in Example 3 on the YSZ. Then the Ni-YSZ/YSZ/LSM sandwich is heated as described in Example 2. Upon heating, the liquid composition will form additional YSZ that will bond the Ni-YSZ disk to the YSZ electrolyte and LSM electrode. The bonded sandwich can be assembled into a fuel cell adapted to supply a hydrogen-containing gas to the Ni-YSZ electrode to act as an anode, and to supply an oxygen-containing gas to the LSM electrode to act as a cathode. Interconnects connecting the anode and cathode to external wiring are adapted to complete the electrical circuit. When the fuel cell is heated to 800° C. and the hydrogen-containing gas and oxygen-containing gas are supplied, the cell should produce electricity, as shown in FIG. 2.

Various embodiments of the invention have been described in fulfillment of the various objects of the invention. It should be recognized that these embodiments are merely illustrative of the principles of the present invention, and do not imply limitation. Furthermore, the foregoing description of various embodiments does not necessarily imply exclusion. For example, "some" embodiments may include all or part of "other" and "further" embodiments. Furthermore, "a" can mean "one or more than one," and does not necessarily mean "one and only one." Numerous modifications and adaptations thereof will be readily apparent to those skilled in the art without departing from the spirit and scope of the invention.

We claim:

1. A method of making an electrolyte for a solid oxide cell comprising at least one metal oxide, comprising:
   applying at room temperature a liquid composition to a substrate that can be adapted to function as an electrode in the solid oxide cell,
   the liquid composition consisting essentially of at least one metal compound, at least one nanoparticle having an average size of 50-100 nm, and optionally at least one carboxylic acid, and
   converting at least some of the at least one metal compound to at least one metal oxide on the substrate,
   wherein the at least one metal compound comprises at least one zirconium compound and at least one yttrium compound.

2. The method of claim 1, further comprising depositing a plurality of metal oxide layers on the substrate.

3. The method of claim 1, further comprising:
   forming a transition layer between the substrate and the at least one metal oxide.

4. The method of claim 3, wherein the transition layer has a thickness ranging from about 3 nm to about 100 nm.

5. The method of claim 4, wherein the transition layer has a thickness less than about 10 nm.

6. The method of claim 1, wherein the at least one zirconium compound comprises zirconium (IV) 2-ethylhexanoate.

7. The method of claim 1, wherein the at least one yttrium compound comprises yttrium (III) 2-ethylhexanoate.

8. The method of claim 1, wherein the at least one metal oxide comprises a plurality of nanocrystalline grains having an average size of less than about 50 nanometers.

9. The method of claim 8, wherein the nanocrystalline grains have an average size of less than about 10 nanometers.

10. The method of claim 1, wherein the substrate comprises at least one catalytic material.

11. The method of claim 10, wherein the at least one catalytic material is chosen from platinum, palladium, rhodium, nickel, cerium, gold, silver, zinc, lead, ruthenium, rhenium, and combinations thereof.

12. The method of claim 2, wherein the plurality of metal oxide layers comprise at least one compositional gradient.

13. The method of claim 12, wherein the compositional gradient comprises substrate material, and the plurality of metal oxide layers comprise a greater concentration of substrate material in a region proximal to the substrate than in a region distal to the substrate.

14. The method of claim 1, wherein the substrate comprises a porous steel alloy.

15. The method of claim 1, wherein the substrate comprises at least one metal, at least one metal carbide, or a combination thereof.

* * * * *